US007544509B2

(12) United States Patent
Toma et al.

(10) Patent No.: US 7,544,509 B2
(45) Date of Patent: *Jun. 9, 2009

(54) METHOD FOR PREPARING STEM CELL PREPARATIONS

(75) Inventors: Jean Toma, Montreal (CA); Mahnaz Akhavan, Montreal (CA); Karl J. L. Fernandes, Montreal (CA); Mathieu Fortier, Orford (CA); Freda Miller, Montreal (CA)

(73) Assignee: McGill University (CA)

( * ) Notice: Subject to any disclaimer, the term of this patent is extended or adjusted under 35 U.S.C. 154(b) by 730 days.

This patent is subject to a terminal disclaimer.

(21) Appl. No.: 10/099,539

(22) Filed: Mar. 15, 2002

(65) Prior Publication Data
US 2003/0003574 A1  Jan. 2, 2003

Related U.S. Application Data

(63) Continuation-in-part of application No. 09/991,480, filed on Nov. 9, 2001, which is a continuation-in-part of application No. 09/916,639, filed on Jul. 26, 2001, now abandoned, which is a continuation-in-part of application No. PCT/CA01/00047, filed on Jan. 24, 2001, and a continuation-in-part of application No. 09/670,049, filed on Sep. 25, 2000, now Pat. No. 6,787,355, which is a continuation-in-part of application No. 09/490,422, filed on Jan. 24, 2000, now abandoned.

(51) Int. Cl.
C12N 5/00 (2006.01)
(52) U.S. Cl. .................. 435/325; 435/368; 435/352; 435/353; 435/354; 424/93.1
(58) Field of Classification Search .................. 435/325
See application file for complete search history.

(56) References Cited

U.S. PATENT DOCUMENTS 5,851,832 A * 12/1998 Weiss et al. .................. 435/368

FOREIGN PATENT DOCUMENTS

| WO | WO 93/01275 | 1/1993 |
| WO | WO 94/09119 | 4/1994 |
| WO | WO 94/10292 | 5/1994 |
| WO | WO 94/16718 | 8/1994 |
| WO | WO 95/12665 | 5/1995 |
| WO | WO 95/13364 | 5/1995 |
| WO | WO 97/41208 | 11/1997 |
| WO | WO 99/56759 | 11/1999 |

OTHER PUBLICATIONS

Shamblott, et al., (1998). Proc. Natl. Acad. Sci. USA 95, 13726 13731.*
Shamblott et al., Proc Natl Acad Sci U S A. Jan. 2, 2001; 98(1): 113-118.*
Freshney, R.I. 1993. Culture of Animal Cells. A Manual of Basic Techniques, 3rd ed. Wiley-Liss, New York pp. 216-225.*
Anderson, D.J. Stem cells and transcription factors in the development of the mammalian neural crest. *FASEB J.* 8, 707-713 (Jul. 1994).
Arsenijevic, Y. & Weiss, S. Insulin-Like Growth Factor-1 is a Differentiation Factor for Postmitotic CNS Stem Cell-Derived Neuronal Precursors: Distinct Actions from Those of Brain-Derived Neurotrophic Factor. *J. Neurosci.* 18, 2118-2128 (Mar. 15, 1998).
Arsenijevic, Y. et al. Insulin-Like Growth Factor-1 is Necessary for Neural Stem Cell Proliferation and Demonstrates Distinct Actions of Epidermal Growth Factor and Fibroblast Growth Factor-2. *J. Neurosci.* 21, 7194-7202 (Sep. 15, 2001).
Auerbach, J.M. et al. Transplanted CNS stem cells form functional synapses in vivo. *Eur. J. Neurosci.* 12, 1696-1704 (May 2000).
Avoli, M. et al. Pharmacology and Electrophysiology of a Synchronous Gaba-Mediated Potential in the Human Neocortex. *Neurosci.* 62, 655-666 (1994).
Bamji, S. et al. Comparison of the Expression of a Talpha1:nlacZ Transgene and Talpha1 alpha-Tubulin mRNA in the Mature Central Nervous System. *J. Comp. Neurol.* 374, 52 (1996).
Bellows, C.G. et al. Determination of Numbers of Osteoprogenitors present in Isolated Fetal Rat Calvaria Cells In Vitro. *Dev. Biol.* 133, 8-13 (1989).
Bjornson, C.R.R. et al. Turning Brain into Blood: A Hematopoietic Fate Adopted by Adult Neural Stem Cells in Vivo. *Science* 283, 534-537 (1999).
Bruckenstein, D.A. & Higgins, D. Morphological Differentiation of Embryonic Rat Sympathetic Neurons in Tissue Culture. *Dev. Biol.* 128, 324-336 (1988).
Brustle, O. et al. Embryonic Stem Cell-Derived Glial Precursors: A Source of Myelinating Transplants. *Science* 285, 754-756 (Jul. 30, 1999).
Burns, S. et al. A primate model of parkinsonism: Selective destruction of dopaminergic neurons in pars compacta of the substantia nigra by N-methyl-4-phenyl-1,2,3,6-tetra-hydropyridine. *PNAS* 80, 4546-4550 (1983).
Calof et al. Analysis of Neurogenesis in a Mammalian Neuroepithelium: Proliferation and Differentiation of an Olfactory Neuron Precursor in Vitro. *Neuron* 3, 315 (1989).
Cameron, H.A. & McKay, R. Stem cells and neutogenesis in the adult brain. *Curr. Opin. Neurobiol.* 8, 677-680 (Oct. 1998).
Carlsson, A. et al. 3,4-Dihydroxyphenylalanine and 5-Hydroxytryptophan as Reserpine Antagonists. *Nature* 180, 1200 (1957).
Clarke, D.L. et al. Generalized Potential of Adult Neural Stem Cells. *Science* 288, 1660-1663 (2000).
Daadi, M. et al. Activin Co-operates with Fibroblast Growth Factor 2 to Regulate Tyrosine Hydroxylase Expression in the Basal Forebrain Ventricular Zone Progenitors. *Neurosci.* 86, 867-880 (Oct. 1998).
Daadi, M.M. & Weiss, S. Generation of Tyrosine Hydroxylase-Producing Neurons form Precursors of the Embryonic and Adult Forebrain. *J. Neurosci.* 19, 4484-4497 (Jun. 1999).

(Continued)

Primary Examiner—David S Romeo
Assistant Examiner—Daniel C Gamett
(74) *Attorney, Agent, or Firm*—Gowling Lafleur Henderson; Hélène D'Iorio

(57) ABSTRACT

This invention relates to multipotent stem cells, purified from the peripheral tissue of mammals, and capable of differentiating into neural and non-neural cell types. These stem cells provide an accessible source for autologous transplantation into CNS, PNS, and other damaged tissues.

10 Claims, 32 Drawing Sheets

OTHER PUBLICATIONS

Dunnet, S.B. et al. Nigral transplants in primate models of parkinsonism. *Intracereb. Transplant. Movem. Disord.*, O. Lindvall, et al., eds. Restorative Neurology 4, 27-51 (1991).

Ehringer, H. et al. Verteilung von noradrenalin und dopamine (3-hydroxytyramin) im gehim des menschen und ihr verhalten bei erkrankungen des extrapyramidalen systems. *Kllin. Wschr.* 38, 1236-1239 (1960).

Fahn, S. Fetal-tissue Transplants in Parkinson's Disease. *N.E. J. Med.* 327, 1589-1590 (1992).

Ferrari, G. et al. Muscle Regeneration by Bone Marrow-Derived Myogenic Progenitors. *Science* 279, 1528-1530 (1998).

Forsberg-Nilsson, K. et al. Platelet-Derived Growth Factor Induces Chemotaxis of Neuroepithelial Stem Cells. *J. Neurosci. Res.* 53, 521-530 (Sep. 1998).

Friachard et al. In vitro differentiation of embryonic stem cells into glial cells and functional neurons. *J. Cell. Sci.* 108, 3181-3185 (1995).

Gage, F.H. et al. Survival and differentiation of adult neuronal progenitor cells transplanted to the adult brain. *PNAS* 92, 11879-11883 (1995).

Gloster, A. et al. The T-alpha1 alpha-Tubulin Promoted Specific Gene Expression as a Function of Neuronal Growth and Regeneration in Transgenic Mice. *J. Neurosci.* 14, 7319-7330 (1994).

Greenwood, A.L. et al. Identification of dividing, determined sensory neuron precursors in the mammalian neural crest. *Development* 126, 3545-3559 (Aug. 1999).

Gussoni, E. et al. Dystrophin expression in the mdx mouse restored by stem cell transplantation. *Nature* 401, 390-394 (1999).

Huard, J.M.T. et al. Adult Olfactory Epithelium Contains Multipotent Progenitors that Give Rise to Neurons and Non-Neural Cells. *J. Comp. Neurol.* 400, 469-486 (Nov. 2, 1998).

Kaufman, S.J. et al. Replicating myoblasts express a muscle-specific phenotype. *PNAS* 85, 9606-9610 (1988).

Keirstead, H.S. et al. Polysialylated Neural Cell Adhesion Molecule-Positive CNS Precursors Generate Both Oligodendrocytes and Schwann Cells to Remyelinate the CNS after Transplantation. *J. Neurosci.* 19, 7529-7536 (1999).

Kessler, P.D. & Byrne, B.J. Myoblast Cell Grafting into Heart Muscle: Cellular Biology and Potential Applications. *Ann. Rev. Physiol.* 61, 219-242 (1999).

LaBonne, C. & Bronner-Fraser, M. Induction and Patterning of the Neural Crest, a Stem Cell-Like Precursor Population. *J. Neurobiol.* 36, 175-189 (1998).

Langston, J.W. et al. Chronic Parkinsonism in Humans Due to a Product of Meperidine-Analog Synthesis. *Science* 219, 979-980 (1983).

Lee, S.H. et al. Efficient generation of midbrain and hindbrain neurons from mouse embryonic stem cells. *Nat. Biotechnol.* 18, 675-679 (Jun. 2000).

LeGal La Salle, G. et al. An Adenovirus Vector for Gene Transfer into Neurons and Glia in the Brain. *Science* 259, 988-990 (1993).

Lumelsky, N. et al. Differentiation of Embryonic Stem Cells to Insulin-Secreting Structures Similar to Pancreatic Islets. *Science* 292, 1389-1394 (May 18, 2001).

Lundberg, C. et al. Survival, Integration, and Differentiation of Neural Stem Cell Lines after Transplantation to the Adult Rat Striatum. *Exp. Neurol.* 145, 342-360 (Jun. 1997).

Mayo, M.L. et al. Desmin expression during early mouse tongue morphogenesis. *Int. J. Dev. Biol.* 36, 255-263 (1992).

McKay, R. Stem Cells in the Central Nervous System. *Science* 276, 66-71 (Apr. 4, 1997).

McKay, R. Stem cells—hype and hope. *Nature* 406, 361-364 (Jul. 27, 2000).

Morrison, S.J. et al. Prospective Identification, Isolation by Flow Cytometry, and In Vivo Self-Renewal of Multipotent Mammalian Neural Crest Stem Cells. *Cell* 96, 737-749 (Mar. 5, 1999).

Morrison, S.J. et al. Transient Notch Activation Initiates an Irreversible Switch from Neurogenesis to Gliogenesis by Neural Crest Stem Cells. *Cell* 101, 499-510 (May 26, 2000).

Morshead, C.M. et al. Neural Stem Cells in the Adult Mammalian Forebrain: A Relatively Quiescent Subpopulation of Subependymal Cells. *Neuron* 13, 1071-1082 (Nov. 1994).

Mujtaba, T. et al. A Common Neural Progenitor for the CNS and PNS. *Dev. Biol.* 200, 1-15 (1998).

Orlic, D. et al. Bone marrow cells regenerate infarcted myocardium. *Nature* 410, 701-705 (Apr. 5, 2001).

Ourednik, v. et al. Developmental Biology: Frontiers for Clinical Genetics. *Clin. Genet.* 56, 267-278 (1999).

Peel, A.L. & Feldman, D.H. Co-localization of glial and neuronal markers in RGF-generated cultures of pluripotent CNS stem cells. *Society Neurosci.* 21, 285:122.6 (1995).

Pereira, R.F. et al. Cultured adherent cells from marrow can serve as long-lasting precursor cells for bone, cartilage, and lung in irradiated mice. *PNAS* 92, 4857-4861 (1995).

Peterson, B.E. et al. Bone Marrow as a Potential Source of Hepatic Oval Cells. *Science* 284, 1168-1170 (1999).

Pittenger, M.F. et al. Multilineage Potential of Adult Human Mesenchymal Stem Cells. *Science* 284, 143-147 (1999).

Prockop, D.J. Marrow Stromal Cells as Stem Cells for Nonhematopoietic Tissues. *Science* 276, 71-74 (1997).

Represa, A. et al. EGF-responsive neural stem cells are a transient population in the developing mouse spinal cord. *Eur. J. Neurosci.* 14, 452-462 (Aug. 2001).

Reynolds, B.A. & Weiss, S. Generation of Neurons and Astrocytes from Isolated Cells of the Adult Mammalian Central Nervous System. *Science* 255, 1707-1710 (1992).

Reynolds, B.A. & Weiss, S. Clonal and Population Analyses Demonstrate that an EGF-Responsive Mammalian Embryonic CNS Precursor is a Stem Cell. *Dev. Biol.* 175, 1-13 (Apr. 10, 1996).

Rietze, R. et al. Mitotically Active Cells that Generate Neurons and Astrocytes are Present in Multiple Regions of the Adult Mouse Hippocampus. *J. Comp. Neurol.* 424, 397-408 (Aug. 28, 2000).

Sanchez-Pernaute, R. et al. In Vitro Generation and Transplantation of Precursor-Derived Human Dopamine Neurons. *J. Neurosci. Res.* 65, 284-288 (Aug. 15, 2001).

Schubert, D. et al. Ontogeny of electrically excitable cells in cultured olfactory epithelium. *PNAS* 82, 7782-7786 (1985).

Shah, N.M. et al. Glial Growth Factor Restricts Mammalian Neural Crest Stem Cells to a Glial Fate. *Cell* 77, 349-360 (May 6, 1994).

Shimazaki, T. et al. The Ciliary Neurotrophic Factor/Leukemia Inhibitory Factor/gp130 Receptor Complex Operates in the Maintenance of Mammalian Forebrian Neural Stem Cells. *J. Neurosci.* 21, 7642-7653 (Oct. 1, 2001).

Sieber-Blum, M. Factors Controlling Lineage Specification in the Neural Crest. *Intl. Rev. Cytol.* 197, 1-33 (2000).

Slack, R.S. & Miller, F.D. Viral vectors for modulating gene expression in neurons. *Curr. Opin. Neural Biol.* 6, 576-583 (1996).

Slack, R.S. et al. Adenovirus-mediated Gene Transfer of the Tumor Suppressor, p53, Induces Apoptosis in Postmitotic Neurons. *J. Cell. Biol.* 135, 1085-1096 (1996).

Soriano, E. et al. Simultaneous Immunocytochemical Visualization of Bromodeoxyuridine and Neural Tissue Antigens. *J. Histochem. Cytochem.* 39, 255-263 (1991).

Sosnowski, E. et al. Chemical traumatization of adult mouse olfactory epithelium in situ stimulates growth and differentiation of olfactory nerves in vitro. *Brain Res.* 702, 37-48 (1995).

Stemple, D.L. & Anderson, D.J. Isolation of a Stem Cell for Neurons and Glia from the Mammalian Neural Crest. *Cell* 71, 973-985 (Dec. 11, 1992).

Studer, L. et al. Transplantation of expanded mesencephalic precursors leads to recovery in parkinsonian rats. *Nat. Neurosci.* 1, 290-295 (Aug. 1998).

Taylor, G. et al. Involvement of Follicular Stem Cells in Forming Not Only the Follicle but Also the Epidermis. *Cell* 102, 451-461 (Aug. 18, 2000).

Tsai, R.Y.L. & McKay, R.D.G. Cell Contact Regulates Fate Choice by Cortical Stem Cells. *J. Neurosci.* 20, 3725-3735 (2000).

Ungerstedt, U. et al. Quantitative Recording of Rotational Behavior in Rats After 6-Hydroxy-Dopamine Lesions of the Nigrostriatal Dopamine System. *Brain Res.* 24, 485-493 (1970).

van der Kooy, D. & Weiss, S. Why Stem Cells? *Science* 287, 1439-1441 (Feb. 25, 2000).

Vescovi, A.L. et al. bFGF Regulates the Proliferative Fate of Unipotent (Neuronal) and Bipotent (Neuronal/Astroglial) EGF-Generated CNS Progenitor Cells. *Neuron* 11, 951-966 (Nov. 1993).

Weiss, S. Pathways for neural stem cell biology and repair. *Nat. Biotechnol.* 17, 850-851 (Sep. 1999).

Weiss, S. et al. Is there a neural stem cell in the mammalian forebrain? *Trends Neurosci.* 19, 387-393 (Sep. 1996).

Weiss, S. et al. Multipotent CNS Stem Cells Are Present in the Adult Mammalian Spinal Cord and Ventricular Neuroaxis. *J. Neurosci.* 16, 7599-7609 (Dec. 1, 1996).

White, P.M. et al. Neural Crest Stem Cells Undergo Cell-Intrinsic Developmental Changes in Sensitivity to Instructive Differentiation Signals. *Neuron* 29, 57-71 (Jan. 2001).

Widner, H. et al. Bilateral fetal mesencephalic grafting in two patients with parkinsonism induced by 1-methyl-4-phenyl-1,2-3,6-tetrahydropyridine (MPTP). *N.E. J. Med.* 327, 1556-1563 (1993).

Winkler, C. et al. EGF-responsive neural progenitor cells, survive, migrate and differentiate after transplantation into the adult rat striatum. *Society for Neurosci.* 21, 2029:796.19 (1995).

Wohl, C.A. & Weiss, S. Retinoic Acid Enhances Neuronal Proliferation and Astroglial Differentiation in Cultures of CNS Stem Cell-Derived Precursors. *J. Neurobiol.* 37, 281-290 (Nov. 5, 1998).

* cited by examiner

ALCIAN BLUE/ALIZARIN RED CO-STAINING REVEALS CALCIUM ACCUMULATIONS WITHIN A LAYER OF CHONDROCYTIC PROTEOGLYCANS

FETAL CARDIAC ACTIN

GFP EXPRESSION

FETAL CARDIAC ACTIN
& HOECSHT

DESMIN

GFP

DESMIN & HOECHST

GFAP　　　　CNP

Smooth Muscle Actin

METHOD FOR PREPARING STEM CELL PREPARATIONS

CROSS REFERENCE TO RELATED APPLICATIONS

This application is a continuation-in-part of and claims priority to U.S. application Ser. No. 09/991,480, filed Nov. 9, 2001, which application is a continuation-in-part of U.S. application Ser. No. 09/916,639, filed Jul. 26, 2001, now abandoned which application is a continuation-in-part of PCT application CA01/00047 filed Jan. 24, 2001 and to U.S. application Ser. No. 09/670,049, filed Sep. 25, 2000, now U.S. Pat. No. 6,787,355 which application is a continuation-in-part of application Ser. No. 09/490,422, filed Jan. 24, 2000, now abandoned each of which is hereby incorporated by reference.

BACKGROUND OF THE INVENTION

The present invention relates to multipotent stem cells (MSCs) purified from peripheral tissues including peripheral tissues containing sensory receptors such as skin, olfactory epithelium, mucosa, and tongue. The invention also relates to cells differentiated from these multipotent stem cells. The invention includes pharmaceutical compositions and uses of either the multipotent stem cells or the differentiated cells derived from such stem cells. Additionally, business methods based on the multipotent stem cells or the differentiated cells are contemplated.

There are a number of diseases of the central nervous system ("CNS") which have a devastating effect on patients. These diseases are debilitating, often incurable, and include, for example, Alzheimer's disease, Huntington's disease, Parkinson's disease, and Multiple Sclerosis.

By way of example, Parkinson's disease is a progressive degenerative disorder of unknown cause. In healthy brain tissue, dopaminergic neurons extend from the substantia nigra of the brain into the neighboring striatum. In Parkinson's disease, these dopaminergic neurons die.

There are a number of methods to treat Parkinson's disease. One method is to treat humans having Parkinson's disease with L-DOPA. A second method is to transplant cells into the substantia nigra or striatum. Transplanted cells replace endogenous cells that are lost as a consequence of disease progression. An animal model of Parkinson's disease is an MPTP-treated non-human primate. The MPTP-treated animals have been transplanted with dopamine-rich embryonic neurons with some success.

To date, the cells used for neural transplant have been collected from the developing brains of aborted fetuses. Aside from the ethical considerations, the method from a practical standpoint is unlikely to provide a sufficient amount of neural tissue to meet the demands. Thus, another source of cells for transplantation is desirable.

Stem cells are undifferentiated cells that exist in many tissues of embryos and adult organisms. In embryos, blastocyst stem cells are the source of cells which differentiate to form the specialized tissues and organs of the developing fetus. In adults, specialized stem cells in individual tissues are the source of new cells, replacing cells lost through cell death due to natural attrition, disease, or injury. Stem cells may be used as substrates for producing healthy tissue where a disease, disorder, or abnormal physical state has destroyed or damaged normal tissue.

Weiss et al., 1996 summarizes the five defining characteristics of stem cells as the ability to:

Proliferate: Stem cells are capable of dividing to produce daughter cells.

Exhibit self-maintenance or renewal over the lifetime of the organism: Stem cells are capable of reproducing by dividing symmetrically or asymmetrically to produce new stem cells. Symmetric division occurs when one stem cell divides into two daughter stem cells. Asymmetric division occurs when one stem cell forms one new stem cell and one progenitor cell. Symmetric division is a source of renewal of stem cells. This permits stem cells to maintain a consistent level of stem cells in an embryo or adult mammal.

Generate large number of progeny: Stem cells may produce a large number of progeny through the transient amplification of a population of progenitor cells.

Retain their multilineage potential over time: Stem cells are the ultimate source of differentiated tissue cells, so they retain their ability to produce multiple types of progenitor cells, which will in turn develop into specialized tissue cells.

Generate new cells in response to injury or disease: This is essential in tissues which have a high turnover rate or which are more likely to be subject to injury or disease, such as the epithelium of blood cells.

Thus, the key features of stem cells are that they are multipotential cells which are capable of long-term self-renewal over the lifetime of a mammal.

MSCs may be used as a source of cells for transplantation. The stem cells may themselves be transplanted or, alternatively, they may be induced to produce differentiated cells (e.g., neurons, oligodendrocytes, Schwann cells, or astrocytes) for transplantation. Transplanted stem cells may also be used to express therapeutic molecules, such as growth factors, cytokines, anti-apoptotic proteins, and the like. Thus, stem cells are a potential source of cells for alternative treatments of diseases involving loss of cells or tissues.

The safest type of tissue graft (using stem cells or otherwise) is one that comes from self (an autologous tissue source). Autologous tissue sources are widely used in procedures such as bone transplants and skin transplants because a source of healthy tissue is readily accessible for transplant to a damaged tissue site. In brain diseases, such as Parkinson's disease, healthy dopaminergic neuronal brain tissue may exist at other sites in the brain, but attempts to transplant these neurons may harm the site where the healthy neurons originate. Multipotent stem cells that can be differentiated into dopaminergic neurons may be available at other sites from which they may be transplanted, but the CNS, particularly the brain, is physically difficult to access.

In several tissues, stem cells have been purified and characterized. For example, neural stem cells have been purified from the mammalian forebrain (Reynolds and Weiss, Science 255:1707-1710, 1992) and these cells were shown to be capable of differentiating into neurons, astrocytes, and oligodendrocytes. PCT publications WO 93/01275, WO 94/16718, WO 94/10292 and WO 94/09119 describe uses for these cells. It could be impractical or impossible, however, to first access brain or other CNS tissue for biopsy and then again for transplant in patients with weakened health. It would be very useful if there were accessible stem cells capable of differentiating into CNS cell types, such as dopaminergic neurons; such cells would be a source of cells for autologous transplants.

Thus, there is a clear need to develop methods for identifying from accessible tissues multipotent stem cells that can act as a source of cells that are transplantable to the CNS, PNS, or other tissues in vivo in order to replace damaged or diseased tissue.

SUMMARY OF THE INVENTION

One aspect of the present invention relates to preparations of purified multipotent stem cells that are obtained from peripheral tissue of mammals, preferably from postnatal mammals such as juvenile and adult mammals. We have identified epithelial tissues, such as skin, as convenient sources of multipotent stem cells, and provide methods for the purification of epithelial-derived MSCs, thus simplifying the harvesting of cells for transplantation relative to previous methods. The MSCs possess desirable features in that they are multipotent and self-renewing. The cells can be repeatedly passaged and can be differentiated into numerous cell types of the body including derivatives of ectodermal and mesodermal tissue. The MSCs of this invention are positive for nestin protein, an immunological marker of stem cells and progenitor cells, as well as fibronectin protein, but are negative for vimentin and cytokeratin when assayed by immunohistochemistry. Moreover, the MSCs of the present invention grow as non-adherent clusters when cultured by the methods herein disclosed, and one of skill in the art will readily recognize that such cells will grow as non-adherent clusters when cultured on a variety of substratum including but not limited to uncoated plastic or plastic coated with a neutral substrate such as gelatin or agar. In certain embodiments, the MSCs of this invention are negative for the neural crest stem cell marker p75. These characteristics distinguish the cells of this invention from other stem cells, including mesenchymal stem cells and neural crest stem cells.

In certain embodiments, the cells are capable of differentiating as dopaminergic neurons, and thus are a useful source of dopaminergic neurons for homotypic grafts into Parkinson's Disease patients. The MSCs can also differentiate as numerous mesodermal derivatives including smooth muscle cells, adipocytes, cartilage, bone, skeletal muscle, and cardiac muscle, and are expected to be capable of producing other mesodermal derivatives including kidney and hematopoietic cells. Additionally, we show that the MSCs can express markers of endodermal differentiation, and are expected to differentiate to cell types including pancreatic islet cells (e.g., alpha, beta, phi, delta cells), hepatocytes, and the like. To our knowledge, the MSCs of the invention represent the first adult stem cell capable of differentiating to cell derived from all three germ layers. The subject cells may also be used for autologous or heterologous transplants to treat, for example, other neurodegenerative diseases, disorders, or abnormal physical states.

Accordingly, in a first aspect, the invention features MSCs substantially purified from a peripheral tissue of a postnatal mammal. In preferred embodiments, the peripheral tissue is an epithelial tissue including skin or mucosal tissue. In a second embodiment, the peripheral tissue is derived from the tongue. In still another embodiment, the tissue is derived from skin. The postnatal mammal may be either a juvenile or adult mammal.

In certain embodiments, the invention features a cell that is the progeny of a MSC substantially purified from a peripheral tissue of a postnatal mammal. The cell may be a mitotic cell or a differentiated cell (e.g., a neuron, an astrocyte, an oligodendrocyte, a Schwann cell, or a non-neural cell). Preferred neurons include neurons expressing one or more of the following neurotransmitters: dopamine, GABA, glycine, acetylcholine, glutamate, and serotonin. Preferred non-neural cells include cardiac muscle cells, pancreatic cells (e.g., islet cells (alpha, beta, phi and delta cells), exocrine cells, endocrine cells, chondrocytes, osteocytes, skeletal muscle cells, smooth muscle cells, hepatocytes, hematopoietic cells, and adipocytes. These non-neural cell types include both mesodermal and endodermal derivatives. In a preferred embodiment, the differentiated cells are substantially purified.

In a second aspect, the invention features a population of at least ten cells, wherein at least 30% of the cells are MSCs substantially purified from a peripheral tissue of a postnatal mammal or progeny of the MSCs.

Preferably, at least 50% of the cells are MSCs substantially purified from the peripheral tissue or progeny of the MSCs. More preferably, at least 75% of the cells are MSCs substantially purified from the peripheral tissue or progeny of the MSCs. Most preferably, at least 90%, 95%, or even 100% of the cells are MSCs substantially purified from the peripheral tissue or progeny of the MSCs. The MSCs may be cultured for extended periods of time. Thus, the population of cells may have been in culture for at least thirty days, sixty days, ninety days, or longer (e.g., one year or more). Preferably, the population is at least twenty cells, and may be more than fifty cells, a thousand cells, or even a million cells or more.

In a third aspect, the invention features preparations of at least ten cells, and more preferably at least $10^4$, $10^5$, $10^6$ or even $10^7$ cells, having less than 25% lineage committed cells. Preferably, less than 20% of the cells are lineage committed cells. More preferably, less than 15% of the cells are lineage committed cells. Most preferably, less than 10%, 5%, or even 0% of the cells are lineage committed cells. In general, any cell feeder layer upon which the cells of the invention are cultured would not be considered in such a calculation.

In a fourth aspect, the invention features a pharmaceutical composition including (i) a mitotic or differentiated cell that is the progeny of a MSC substantially purified from a peripheral tissue of a postnatal mammal, and (ii) a pharmaceutically acceptable carrier, auxiliary or excipient.

In a fifth, related aspect, the invention features a pharmaceutical composition including (i) a MSC substantially purified from a peripheral tissue of a postnatal mammal, and (ii) a pharmaceutically acceptable carrier, auxiliary or excipient.

Preferably, the composition of the fourth or fifth aspect includes a population of cells, wherein at least 30%, 50%, 75%, 90%, 95%, or even 100% of the cells are MSCs substantially purified from the peripheral tissue or progeny of the MSCs. The composition may include one or more types of cells selected from a group consisting of MSCs, or neurons, oligodendrocytes, Schwann cells, astrocytes, adipocytes, smooth muscle cells, cardiomyocytes, chondrocytes, osteocytes, skeletal muscle cells, hepatocytes, hematopoietic cells, exocrine cells, endocrine cells and alpha, beta, phi and delta cells, which are progeny of MSCs.

In a sixth aspect, the invention features a method of producing a population of at least ten cells, wherein at least 30% of the cells are MSCs substantially purified from a peripheral tissue of a postnatal mammal or progeny of the MSCs: (a) providing the peripheral tissue from the mammal; (b) culturing the tissue under conditions in which MSCs proliferate and in which at least 25% of the cells that are not MSCs die; and (c) continuing culture step (b) until at least 30% of the cells are MSCs or progeny of the MSCs.

In a seventh aspect, the invention features another method of producing a population of at least ten cells, wherein at least 30% of the cells are MSCs substantially purified from skin tissue of a postnatal mammal or progeny of the MSCs, the method including: (a) providing the skin tissue from the mammal; (b) culturing the tissue under conditions in which MSCs proliferate and in which at least 25% of the cells that are not MSCs die; (c) separating the MSCs from cells that are not MSCs based on the tendency of MSCs to form non-adherent clusters; and (d) repeating steps (b) and (c) until at least 30% of the cells are MSCs or progeny of the MSCs.

Suitable culture conditions for step (b) of the sixth and seventh aspects are preferably as follows: (i) triturating or otherwise separating tissue into single cells or cell clusters and placing into culture medium; (ii) culturing the cells in culture medium and under conditions (e.g., DMEM: Ham's F-12 medium containing B-27 supplement, antibacterial and antifungal agents, 5-100 ng/ml bFGF, and 2-100 ng/ml EGF) that allows for the proliferation of MSCs but does not promote, to the same extent, proliferation of cells that are not MSCs; and (iii) culturing the separated tissue for three to ten days, during which time the MSCs proliferate in suspension and form non-adherent clusters but non-MSCs do not proliferate in suspension (these cells either attach to the plastic or they die). Preferably, at least 50% of the cells in suspension surviving after the period in culture are MSCs or progeny of the MSCs, more preferably, at least 75% of the cells are MSCs or progeny of the MSCs, and, most preferably, at least 90% or even 95% of the surviving cells are MSCs or progeny of the MSCs. In preferred embodiments, tissue is separated mechanically.

In an eighth aspect, the invention features a method of treating a patient having a disease associated with cell loss. In one embodiment, the method includes the step of transplanting the multipotent stem cells of the invention into the region of the patient in which there is cell loss. Preferably, prior to the transplanting step, the method includes the steps of providing a culture of peripheral tissue and isolating a multipotent stem cell from the peripheral tissue. The tissue may be derived from the same patient (autologous) or from either a genetically related or unrelated individual. After transplantation, the method may further include the step of differentiating (or allowing the differentiation of) the MSCs into a desired cell type to replace the cells that were lost. Preferably, the region is a region of the CNS or PNS, but can also be cardiac tissue, pancreatic tissue, or any other tissue in which cell transplantation therapy is possible. In a second embodiment, the method includes the step of delivering the stem cells to the site of cell damage via the bloodstream, wherein the stem cells home to the site of cell damage. In a third embodiment, the method for treating a patient includes the transplantation of the differentiated cells which are the progeny of the stem cells of this invention.

In a ninth aspect, the invention features a kit including MSCs substantially purified from peripheral tissue of a postnatal mammal, or a mitotic or differentiated cell that is the progeny of the MSC, preferably wherein the peripheral tissue from which the MSC is purified includes a sensory receptor. Preferably, the kit includes a population of cells, wherein at least 30%, 50%, 75%, 90%, or even 95% of the cells are MSCs substantially purified from the peripheral tissue or progeny of the MSCs.

In a tenth aspect, the invention features a kit for purifying MSCs from peripheral tissue. The kit includes media or media components that allow for the substantial purification of MSCs of the present invention. The kit may also include media or media components that allow for the differentiation of the MSCs into the desired cell type(s). Preferably, the kit also includes instructions for its use. In one embodiment, the media includes one or more therapeutic proteins, pharmaceutical agents, and/or small molecules that influence the proliferation, differentiation, and/or survival of the MSCs.

In one preferred embodiment of each of the foregoing aspects of the invention, the peripheral tissue is skin tissue. In another preferred embodiment, the peripheral tissue is tongue tissue, hair follicles, sweat glands, or sebaceous glands. In another preferred embodiment of each of the foregoing aspects of the invention, the stem cells are negative for p75.

The peripheral tissue can be from a newborn mammal, a juvenile mammal, or an adult mammal. Preferred mammals include, for example, humans, non-human primates, mice, pigs, and rats. The MSCs can be derived from peripheral tissue of any individual, including one suffering from a disease or from an individual immunologically compatible to an individual suffering from a disease. In a preferred embodiment, the cells, or progeny of the cells, are transplanted into the CNS or PNS of an individual having a neurodegenerative disease and the individual is the same individual from whom the MSCs were purified. Following transplantation, the cells can differentiate into cells that are lacking or nonfunctional in the disease.

Preferably, the MSCs are positive for nestin and fibronectin protein and may also express glutamic acid decarboxylase, but are negative for vimentin and cytokeratin protein. The MSCs of the present invention can, under appropriate conditions, differentiate into neurons, astrocytes, Schwann cells, oligodendrocytes, and/or non-neural cells (e.g., cardiac muscle cells, skeletal muscle cells, pancreatic cells, smooth muscle cells, adipocytes, hepatocytes, cartilage, bone, etc.). In a preferred embodiment, the differentiated neurons are dopaminergic neurons. In a preferred embodiment, the differentiated non-neural cells are selected from smooth muscle cells, adipocytes, cartilage, bone, skeletal muscle, or cardiac muscle.

We show that the MSCs of the invention have tremendous capacity to differentiate into a range of neural and non-neural cell types. The non-neural cell types include both mesodermal and endodermal derivatives. The MSCs of the invention thus provide an adult stem cell capable of differentiating to derivatives of all three germ layers. This capacity can be further influenced by modulating the culture conditions to influence the proliferation, differentiation, and survival of the MSCs. In one embodiment, modulating the culture conditions includes increasing or decreasing the serum concentration. In another embodiment, modulating the culture conditions includes increasing or decreasing the plating density. In still another embodiment, modulating the culture conditions includes the addition of one or more pharmacological agents to the culture medium. In another embodiment, modulating the culture conditions includes the addition of one or more therapeutic proteins (i.e., growth factors, cytokines, anti-apoptotic proteins) to the culture medium. In still another embodiment, modulating the culture conditions includes the addition of one or more small molecules that agonize or antagonize the function of a protein involved in cell proliferation, differentiation, or survival. In each of the foregoing embodiments, pharmacological agents, therapeutic proteins, and small molecules can be administered individually or in any combination, and combinations of any of the pharmaceutical agents, therapeutic proteins, and small molecules can be coadministered or administered at different times.

MSCs can be stably or transiently transfected with a heterologous gene (e.g., one encoding a therapeutic protein, such as a protein which enhances cell divisions or prevents apoptosis of the transformed cell or other cells in the patient, or a cell fate-determining protein). In one embodiment, the heterologous gene modulates one or more of cell proliferation, differentiation, or survival. In preferred embodiments, transfection of the heterologous gene is adenoviral mediated. In another preferred embodiment, transfection occurs using standard protocols for transfection in cell culture including lipofectamine mediated transfection or electroporation.

In an eleventh aspect, the invention features preparations of stem cells and their differentiated progeny preserved for subsequent retrieval. In one preferred embodiment, the preserved cells are formulated in a pharmaceutically acceptable carrier. In another embodiment, the stem cells or differentiated progeny are preserved using cryogenic methods.

In a twelfth aspect, the invention features a method for conducting a regenerative medicine business. In one embodiment, the method comprises accepting and cataloging tissue samples from a client, culturing the cells from said sample to expand the multipotent stem cells, preserving such cells and storing them for later retrieval. In a second embodiment, the method comprises accepting and cataloging tissue samples from a client, culturing the cells from said sample to expand the multipotent stem cells, and differentiating the stem cell. Both of these embodiments also contemplate a billing system for billing the client or an insurance provider.

In a thirteenth aspect, the invention features a method for conducting a stem cell business comprising identifying agents which influence the proliferation, differentiation, or survival of the multipotent stem cells of the invention. Such agents include small molecules and extracellular proteins. In a preferred embodiment, the identified agents could be profiled and assessed for safety and efficacy in animals. In another preferred embodiment, the invention contemplates methods for influencing the proliferation, differentiation, or survival of the multipotent stem cells of the invention by contacting the cells with an agent or agents identified by the foregoing method. In another preferred embodiment, the identified agents are formulated as a pharmaceutical preparation. This pharmaceutical preparation can be manufactured, marketed, and distributed for sale.

In a fourteenth aspect, the invention includes a method for conducting a drug discovery business comprising identifying factors which influence the proliferation, differentiation, or survival of the multipotent stem cells of the invention, and licensing the rights for further development.

In the foregoing aspects of the invention, it is appreciated that the MSCs of the invention can proliferate in culture, and differentiate to derivatives of all three germ layers. Therefor, the MSCs provide novel compositions of adult stem cells which have therapeutic applications in treating conditions which affect wide range of cell types derived from all three germ layers. Recognizing the ability of these cells to differentiate to derivatives of all three germ layers, in a fifteen aspect, the invention includes a cellular composition of adult stem cells which (i) will proliferate in an in vitro culture, (ii) maintains the potential to differentiate to derivatives of endoderm, mesoderm, and ectoderm tissues throughout the culture, and (iii) is inhibited from differentiation when cultured under proliferative conditions.

Furthermore, in a sixteenth aspect, the invention includes a cellular composition of adult stem cells which (i) will proliferate in an in vitro culture for over one year, (ii) maintains a karyotype in which the chromosomes are euploid and not altered through prolonged culture, (iii) maintains the potential to differentiate to derivatives of endoderm, mesoderm, and ectoderm tissues throughout the culture, and (iv) is inhibited from differentiation when cultured under proliferative conditions.

For convenience, certain terms employed in the specification, examples, and appended claims are collected here.

By "multipotential stem cell" is meant a cell that (i) has the potential of differentiating into at least two cell types selected from a neuron, an astrocyte, and an oligodendrocyte, and (ii) exhibits self-renewal, meaning that at a cell division, at least one of the two daughter cells will also be a stem cell. The non-stem cell progeny of a single MSC are capable of differentiating into neurons, astrocytes, Schwann cells, and oligodendrocytes. Hence, the stem cell is "multipotent" because its progeny have multiple differentiative pathways. The MSC also has the potential to differentiate as another non-neuronal cell type (e.g., a skin cell, a hematopoietic cell, a smooth muscle cell, a cardiac muscle cell, a skeletal muscle cell, a bone cell, a cartilage cell, a pancreatic cell or an adipocyte).

By a "population of cells" is meant a collection of at least ten cells. Preferably, the population consists of at least twenty cells, more preferably at least one hundred cells, and most preferably at least one thousand or even one million cells. Because the MSCs of the present invention exhibit a capacity for self-renewal, they can be expanded in culture to produce populations of even billions of cells.

By "substantially purified" is meant that the desired cells (e.g., MSCs) are enriched by at least 30%, more preferably by at least 50%, even more preferably by at least 75%, and most preferably by at least 90% or even 95%.

By "therapeutic protein" is meant a protein that improves or maintains the health of the cell expressing the protein or of a cell that is in proximity to the expressing cell. The term therapeutic protein shall encompass any protein that influences the proliferation, differentiation, and/or survival of the cells of the invention, without regard to the mechanism by which the therapeutic protein has this effect. Examples of therapeutic proteins include, without limitation, growth factors (NGF, BDNF, NT-3, NT-4/5, HGF, TGF-β family members, PDGF, GDNF, FGF, EGF family members, IGF, insulin, BMPs, Wnts, hedgehogs, and heregulins) cytokines (LIF, CNTF, TNFµ interleukins, and gamma-interferon), and anti-apoptotic proteins (IAP proteins, Bcl-2 proteins, Bcl-$X_L$, Trk receptors, Akt, PI3 kinase, Gab, Mek, E1B55K, Raf, Ras, PKC, PLC, FRS2, rAPs/SH2B, and Np73). Additionally, therapeutic proteins include receptors for and the intracellular components of signal transduction pathways. These signal transduction pathway are well known in the art (hedgehog pathway, Wnt pathway, BMP pathway, Notch pathway, FGF, etc), and one of skill will recognize that expression and/or treatment with components (ligands, receptors, or intracellular components) of a signal transduction pathway can modulate signaling via that pathway with subsequent effects on cell proliferation, differentiation, and/or survival.

By "small molecule" is meant a compound having a molecular weight less than about 2500 amu, preferably less than about 2000 amu, even more preferably less than about 1500 amu, still more preferably less than about 1000 amu, or most preferably less than about 750 amu. "Small organic molecule" are those small molecules which contain carbon.

By "plating conditions" is meant to include any and all parameters that influence the proliferation, differentiation, and/or survival of cells. Plating conditions include, but are not limited to, changes in serum concentration, changes in plating density, the use of various feeder layers and co-cultures, the addition of therapeutic proteins to the culture media, the addition of small molecules to the culture media, the addition of pharmacological agents to the culture media, and the addition of metals to the culture media. Any of these parameters may be altered individually or in combination, and combinations of these parameters can be manipulated at the same time or at different times. Additionally, it is understood, that the MSCs can be sorted prior to plating, such that a sub-population of MSCs are subjected to the differentiation conditions. Sorting of the MSCs may be based on the expression (or lack of expression) of a gene or protein. Furthermore, sorting of the MSCs may be based on cellular characteristics including cell adhesion, or morphology.

By "peripheral tissue" is meant a tissue that is not derived from neuroectoderm, for example peripheral tissue containing sensory receptors, and specifically includes olfactory epithelium, tongue, skin (including dermis and/or epidermis), and mucosal layers of the body (e.g., mouth, reproductive system).

By "epithelia" and "epithelium" in meant the cellular covering of internal and external body surfaces (cutaneous, mucous and serous), including the glands and other structures derived therefrom, e.g., corneal, esophegeal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, that which is characteristically found lining hollow organs that are subject to great mechanical change due to contraction and distention, e.g. tissue which represents a transition between stratified squamous and columnar epithelium. The term "epithelialization" refers to healing by the growth of epithelial tissue over a denuded surface.

By "skin" is meant the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

By "epidermis" is meant the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, conified non-nucleated cells. In the epidermis of the general body surface, the clear layer is usually absent. An "epidermoid" is a cell or tissue resembling the epidermis, but may also be used to refer to any tumor occurring in a noncutaneous site and formed by inclusion of epidermal elements.

By "ectoderm" is meant the outermost of the three primitive germ layers of the embryo; from which are derived the epidermis and epidermal tissues such as the nails, hair and glands of the skin, the nervous system, external sense organs and mucous membrane of the mouth and anus.

By "mesoderm" is meant the middle of the three primitive germ layers of the embryo; from which are derived the heart, kidney, skeletal muscle, bone, cartilage, blood, endothelial lining of blood vessels, adipose tissue, and the urogenital system.

By "endoderm" is meant the innermost of the three primitive germ layers of the embryo; from which are derived the lungs, trachea, pharynx, thyroid, pharyngeal pouch derivatives, and the organs of the gut including the stomach, small intestines, large intestines, pancreas, liver, gall bladder, appendix, esophagus, rectum, anus, and urinary bladder.

By "differentiation" is meant the formation of cells expressing markers known to be associated with cells that are more specialized and closer to becoming terminally differentiated cells incapable of further division or differentiation.

By "lineage committed cell" is meant a progenitor cell that is no longer pluripotent but has been induced to differentiate into a specific cell type, e.g., a dopaminergic neuron.

By "proliferation" is meant an increase in cell number.

By "non-adherent clusters" is meant that the cells of the invention are able to adhere to each other and form clusters which increase in size as the cells proliferate, but these cells do not adhere to the substratum and grow in suspension, wherein the substratum is uncoated tissue culture plastic or a culture vessel coated with a neutral coating such as agar or gelatin.

By "dissociating a sample" is meant to separate tissue into either single cells, smaller cell clusters, or smaller pieces of tissue.

By "postnatal" is meant an animal that has been born at term.

By "a disease characterized by failure of a cell type" is meant one in which the disease phenotype is the result of loss of cells of that cell type or the loss of function of cells of that cell type.

By "autologous transplant" is meant that the transplanted material (e.g., MSCs or the progeny or differentiated cells thereof) is derived from and transplanted to the same individual.

By "nucleic acid" is meant polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

By "gene" is meant a nucleic acid comprising an open reading frame encoding a polypeptide, including both exon and (optionally) intron sequences.

By "transfection" is meant the introduction of a nucleic acid, e.g., an expression vector, into a recipient cell by nucleic acid-mediated gene transfer.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. It will also be understood that the recombinant gene can be under the control of transcriptional regulatory sequences which are the same or which are different from those sequences which control transcription of the naturally-occurring gene.

By "tissue-specific promoter" is meant a DNA sequence that serves as a promoter, i.e., regulates expression of a selected DNA sequence operably linked to the promoter, and which effects expression of the selected DNA sequence in specific cells of a tissue, such as cells of neuronal or hematopoietic origin. The term also covers so-called "leaky" promoters, which regulate expression of a selected DNA primarily in one tissue, but can cause at least low level expression in other tissues as well.

Other features and advantages of the present invention will become apparent from the following detailed description and the claims. It will be understood, however, that the detailed description and the specific examples, while indicating preferred embodiments of the invention, are given by way of example only, and various changes and modifications within the spirit and scope of the invention will become apparent to those skilled in the art from this detailed description.

DETAILED DESCRIPTION OF THE INVENTION

Figure 1A:
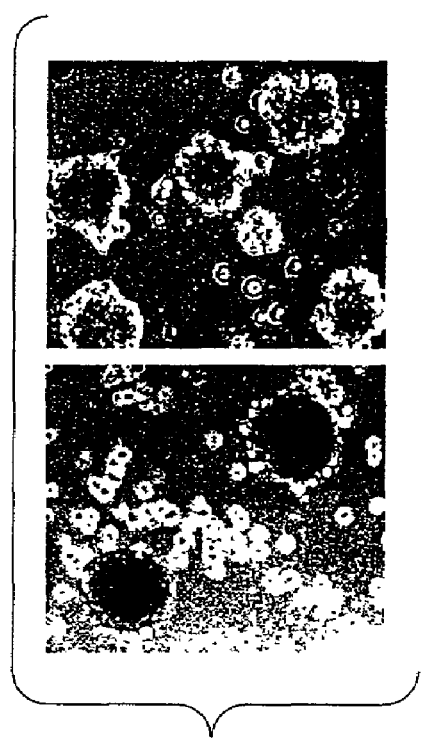
FIGS. 1A-1G are photographs showing that mouse skin-derived MSCs are nestinpositive and are capable of differentiating into neurons, glia, and smooth muscle cells.

We have substantially purified multipotent stem cells (MSCs) from peripheral tissues of mammals, including skin, olfactory epithelium, and tongue. These cells proliferate in culture, so that large numbers of stem cells can be generated. These cells can be induced to differentiate, for example, into neurons, astrocytes, and/or oligodendrocytes by altering the culture conditions. They can also be induced to differentiate into non-neural cells such as smooth muscle cells, cartilage, bone, skeletal muscle, cardiac muscle, and adipocytes. The substantially purified neural stem cells are thus useful for generating cells for use, for example, in autologous transplants for the treatment of degenerative disorders or trauma (e.g., spinal cord injury). In one example, MSCs may be differentiated into dopaminergic neurons and implanted in the substantia nigra or striatum of a Parkinson's disease patient. In a second example, the cells may be used to generate oligodendrocytes for use in autologous transplants for the treatment of multiple sclerosis. In a third example, the MSCs may be used to generate Schwann cells for treatment of spinal cord injury, cardiac cells for the treatment of heart disease, or pancreatic islet cells for the treatment of diabetes. In a fourth example, MSCs may be used to generate adipocytes for the treatment of anorexia or wasting associated with many diseases including AIDS, cancer, and cancer treatments. In a fifth example, MSCs may be used to generate smooth muscle cells to be used in vascular grafts. In a sixth example, MSCs may be used to generate cartilage to be used to treat cartilage injuries and degenerative conditions of cartilage. In still another example, MSCs may be used to replace cells damaged or lost to bacterial or viral infection, or those lost to traumatic injuries such as burns, fractures, and lacerations. If desired, in any of the foregoing examples, the cells may be genetically modified to express, for example, a growth factor, an anti-apoptotic protein, or another therapeutic protein. Similarly, the proliferation, differentiation, or survival of the MSCs of the invention can be influenced by modulating the cell culture conditions including increasing or decreasing the concentration of serum in the culture medium and increasing or decreasing the plating density. Additionally, modulating the cell culture conditions includes contacting the MSCs (by adding to the culture medium) with an agent or agents that influence proliferation, differentiation, or survival. Exemplary agents include therapeutic proteins (i.e., growth factors, cytokines, cell-fate determining proteins, and anti-apoptotic factors), small molecules which may agonize or antagonize the effects of any of the foregoing proteins, and pharmacological agents. In one embodiment, the MSCs are presorted prior to plating and differentiation such that only a sub-population of MSCs are subjected to the differentiation conditions. Presorting of the MSCs can be done based on expression (or lack of expression) of a gene or protein, or based on differential cellular properties including adhesion and morphology.

The MSCs display some similarities to stem cells derived from mammalian forebrain, but also possess some distinctive differences. Firstly, non-adherent clusters of the proliferating MSCs of the invention are morphologically distinct from CNS derived neurospheres. Additionally, when the MSCs of the present invention differentiate in the presence of serum, about 5-20% of the differentiated cells express neuronal markers, whereas differentiated forebrain stem cells generate only a small percentage of neurons. Moreover, significant numbers of dopaminergic neurons are found in differentiated cultures of MSCs of the present invention, whereas such neurons have not been observed in cultures of forebrain stem cells differentiated in serum. Furthermore, we have not observed any significant effects on the proliferation, differentiation or survival of the stem cells of the present invention when cultured in the presence versus the absence of LIF. Thus, the MSCs of the invention represent a novel stem cell population which can differentiate to form both neural and non-neural cell types.

Cell Therapy

The multipotent stem cells of this invention may be used to prepare pharmaceutical compositions that can be administered to humans or animals for cell therapy. The cells may be undifferentiated or differentiated prior to administration. Dosages to be administered depend on patient needs, on the desired effect, and on the chosen route of administration.

The invention also features the use of the cells of this invention to introduce therapeutic compounds into the diseased, damaged, or physically abnormal CNS, PNS, or other tissue. The MSCs thus act as a vector to transport the compound. In order to allow for expression of the therapeutic compound, suitable regulatory elements may be derived from a variety of sources, and may be readily selected by one with ordinary skill in the art. Examples of regulatory elements include a transcriptional promoter and enhancer or RNA polymerase binding sequence, and a ribosomal binding sequence, including a translation initiation signal. Additionally, depending on the vector employed, other genetic elements, such as selectable markers, may be incorporated into the recombinant molecule. The recombinant molecule may be introduced into the stem cells or the cells differentiated from the stem cells using in vitro delivery vehicles such as retroviral vectors, adenoviral vectors, DNA virus vectors and liposomes. They may also be introduced into such cells in vivo using physical techniques such as microinjection and electroporation or chemical methods such as incorporation of DNA into liposomes. Such standard methods can be used to either transiently or stably introduce heterologous recombinant molecules into the cells. The genetically altered cells may be encapsulated in microspheres and implanted into or in proximity to the diseased or damaged tissue.

In one embodiment, the MSCs are used for the treatment of neurological disease. In another aspect the MSCs of the present invention may also be used as a source of non-neural cells, for example adipocytes, bone, cartilage, and smooth muscle cells. As an example, PCT publication WO99/16863 describes the differentiation of forebrain MSCs into cells of the hematopoietic cell lineage in vivo, The MSCs of the present invention appear to be more plastic and thus are highly likely to also be capable of differentiating into non-neural cell types, such as hematopoietic cells. Accordingly, the invention features methods of treating a patient having any disease or disorder characterized by cell loss by administering MSCs of the present invention (or cells derived from these cells) to that patient and allowing the cells to differentiate to replace the cells lost in the disease or disorder. For example, transplantation of MSCs and their progeny provide an alternative to bone marrow and hematopoietic stem cell transplantation to treat blood-related disorders. Other uses of the MSCs are described in Ourednik et al. (Clin. Genet. 56:267-278, 1999), hereby incorporated by reference. MSCs and their progeny provide, for example, cultures of adipocytes and smooth muscle cells for study in vitro and for transplantation. Adipocytes secrete a variety of growth factors that may be desirable in treating cachexia, muscle wasting, and eating disorders. Smooth muscle cells may be, for example, incorporated into vascular grafts, intestinal grafts, etc. Cartilage cells have numerous orthopedic applications to treat cartilage injuries (i.e., sports injuries), as well as degenerative diseases and osteoarthritis. The cartilage cells can be used alone, or in combination with matrices well known in the art. Such matrices are used to mold the cartilage cells into requisite shapes.

Transplantation and delivery of MSC's and their progeny may be at the actual site of cell damage or via the blood stream.

The following examples describe (i) the derivation of MSCs from postnatal and adult mouse and rat tissue, (ii) the derivation of MSCs from human tissue, (iii) the differentiation of MSCs in vitro to both ectodermal and mesodermal derivatives, (iv) clonal analysis demonstrating that single MSCs are multipotent, (v) the effects of modulating culture conditions on the proliferation, differentiation, and survival of MSCs, (vi) the transformation of MSCs with exogenous DNA, (vii) the in vivo differentiation of MSCs following transplantion.

EXAMPLE 1

Purification of MSCs from Postnatal Mouse Olfactory Epithelium

MSCs from mouse olfactory epithelium were purified as described below. Postnatal mice were stunned with a blow to the head and then decapitated. The heads were sagitally sectioned with a razor blade, and the olfactory epithelia of about six postnatal (P1-P9) mouse pups were stripped from the conchae, nasal septum, and vomeronasal organs using watchmaker forceps. This tissue was placed into 3 mL of medium (DMEM/F-12 3:1) supplemented with 2% B-27 (Gibco, Burlington, Ontario, Canada), 20 ng/mL epidermal growth factor (EGF; Collaborative Research, Bedford, Mass.), 0.1% fungizone, and 0.5 mL/100 mL penicillin/streptomycin (Gibco). Following collection, the epithelia were teased apart with watchmaker forceps, releasing a large number of single cells and small cell clusters. The cell suspension was transferred to a 15 mL tube, and 7 mL of additional medium was added. The clusters were dissociated into single cells by manual titration with a 10 mL plastic pipette and passed through a 60 micron filter (Gibco). Typically, dissociated cells from the olfactory epithelia from six pups were plated into two 50 mL tissue culture flasks and cultured in a 37° C., 5% $CO_2$ tissue culture incubator. Two days later, most cells in the cultures were dead or dying. A small number (less than 1% of the initial cell number) of large, phase bright cells were present, however, most of which were attached to the flask bottom. Over the next two to six days, these cells divided and produced spherical clusters, which became larger over time. At four to five days in culture, there were approximately 500 clusters of dividing cells per pup used in the original purification. Most of these cell clusters detached from the flask surface over the next few days. These non-adherent cell clusters continued to grow and fused together to become macroscopic, reaching approximately 100 µm in diameter following 10 DIV. After 12 DIV, the non-adherent cell clusters became macroscopic, reaching approximately 200 µm or greater in diameter.

If EGF was not added to the medium, small clusters of dividing cells were still seen by 4 DIV, indicating that the cells themselves were producing trophic factors in quantities that, in some cases, was sufficient to maintain their proliferation.

Greater than 95% of the cells in the dividing clusters expressed nestin, a marker for stem cells and neural stem cells. These nestin-positive cells could be repeatedly passaged, indicating that the cells were stem cells. Six days after purification, the medium (5 mL) was removed from the flasks. This medium contained many clusters of non-adherent stem cells that had detached from the flask surface. The detached cells clusters were manually triturated with a fire-polished pipette, thereby dissociating many of the cell clusters into single cells. The medium containing the cells was then placed in a second flask with an additional 15 mL of fresh medium (total volume=20 mL). After a further six days, one quarter of the medium was removed and the non-adherent clusters of cells were again triturated and transferred to a new flask with 15 mL fresh medium. These cells have been successfully passaged more than twenty times without losing their multipotency.

EXAMPLE 2

Differentiation of Mouse MSCs into Neurons, Astrocytes and Oligodendrocytes

After the cellular clusters of Example 1 had been generated, they could be differentiated into neurons, astrocytes, and oligodendrocytes. Clusters from cultures 7 to 14 days after purification were plated onto polylysine coated 35 mm culture dishes or 4 multiwell culture dishes, in DMEM/F12 media containing 2% fetal bovine serum (Hyclone, Logan, Utah) and 2% B-27 (containing no EGF). The medium was changed every three to four days. Over the next six to nineteen days, cells migrated out of the clusters onto the dish surface. Some of these cells had the morphology of neurons, astrocytes, or oligodendrocytes. We determined the phenotype of these cells using the following antibodies: GFAP for astrocytes; neurofilament 160 (NF-160), MAP-2, βIII tubulin, and NeuN for neurons; and GC for oligodendrocytes. Antibodies to tyrosine hydroxylase (TH) were used to identify dopaminergic, noradrenergic, and adrenergic neurons. Dopamine-hydroxylase (DBH) was also used for noradrenergic and adrenergic neurons.

Astrocytes, neurons, and oligodendrocytes were all found to differentiate from the MSCs of this invention, indicating that the cells were multipotent. We also cultured MSCs from transgenic mice which express β-galactosidase off of the neuron specific T1 α-tubulin promoter, which allowed us to use staining with the ligand X-gal or antibodies for β-galactosidase as an additional neuronal marker. We observed β-galactosidase-positive cells.

Since the majority of differentiated cells remained in clusters, it was not possible to determine the percentage of cells expressing each marker. The majority of cells that migrated out of the clusters were GFAP positive, while a large number of cells were either NeuN or β-galactosidase positive. A lower number of cells were GC positive. Therefore the MSCs could differentiate into neurons, astrocytes and oligodendrocytes. TH-positive cells were also identified. These TH-positive cells are most likely dopaminergic neurons and not noradrenergic or adrenergic neurons, since no cells were found to be DBH positive. Significantly, no TH, GFAP or GC positive cells have ever been reported in vivo in the nasal epithelium. Therefore the olfactory epithelium-derived nestin-positive MSCs are capable of differentiating into cell types (e.g., oligodendrocytes, astrocytes, GABAergic neurons, and dopaminergic neurons) never found in the olfactory epithelium.

Like the originally-purified olfactory MSCs, MSCs passaged from two to twenty times could also differentiate into neurons, astrocytes, and oligodendrocytes. MSCs which had been passaged were plated on polylysine-coated dishes. Cells migrated from the clusters and spread out over the surface of the dish. After 16 DIV, cells that were immunopositive for GC, GFAP, βIII tubulin, NeuN, lacZ, or TH could be identified. Moreover, the proportion of cells positive for the various markers was similar to that seen in the differentiated cultures from the original cultures.

EXAMPLE 3

Purification of MSCs from Olfactory Epithelial Tissue of Adult Mice and Rats

Similar to the foregoing results, MSCs were also purified from adult mouse and rat olfactory epithelium and vomeronasal organ using the methods described in Examples 1 and 2.

Adult mice and rats were anaesthetized with an overdose of somnitol, and then decapitated. The olfactory and vomeronasal organ epithelia were stripped from the conchae and nasal septum and incubated in DMEM/F12 medium for one to two days after their dissection and prior to the rest of the purification procedure. After this incubation, the epithelia were dissociated in an identical manner as the epithelia from juvenile mice. Two days after the isolation, the majority of the cells were dead with the exception of a very few large phase bright cells. These cells divided over the next few days, forming small clusters of dividing cells similar to those described in Example 1. These small clusters grew to give rise to the large clusters that detached from the culture dish surface. After approximately six divisions, cells in some of these clusters began to differentiate and spread out over the flask's surface, while some other clusters, which had been floating, reattached to the surface and then produced differentiated cells. In some cases, cells multiplied to produce small clusters of cells, but did not grow to form large cell clusters like the postnatal cultures. We have passaged these cells twenty times using the same procedure as that described above with respect to the cells purified from juvenile olfactory epithelium. These proliferating cells from the adult were also nestin-positive.

After the cell clusters derived from adult tissue had been generated, the cells could be differentiated into neurons, astrocytes, and oligodendrocytes. Seven days after isolation, clusters were plated onto polylysine-coated 35 mm culture dishes or multi-well culture dishes, in medium containing 2% fetal bovine serum and 2% B-27, but no EGF. Over the next month, cells migrated from the cell clusters and onto the dish surface. We determined the phenotype of these cells using antibodies to astrocytes, neurons, dopaminergic neurons, and oligodendrocytes as described above.

Neurons (including dopaminergic neurons), astrocytes, and oligodendrocytes were found, although the number of these cells was much lower than the number obtained from the juvenile. The cells purified from adult olfactory epithelia are self-renewing and multipotent, and thus are MSCs.

EXAMPLE 4

Purification of MSCs from Mouse Tongue

We derived MSCs from the tongue, another peripheral tissue that contains sensory receptors. The tongue was dissected to remove the epithelial layer that contains the sensory receptors and their underlying basal cells. This layer of tissue was triturated to produce single cells and the single cells were plated in flasks containing DMEM/F12 media supplemented with B-27 and EGF, TGF, and/or bFGF, as described for the olfactory epithelium. After two to three days in a 37° C., 5% $CO_2$ tissue culture incubator, greater than 99% of the cells in the culture were dead or dying. A small number (less than 1%) of large phase-bright cells were present, however, most of which attached to the flask bottom. Over the next two to six days, these cells divided and produced spherical clusters that became larger over time and detached from the flask surface. The cells in these clusters were nestin-positive.

These nestin-positive MSCs can be passaged using the same techniques as used for the multipotent stem cells derived from the olfactory epithelium. Similarly, the MSCs can be differentiated into neurons, astrocytes and oligodendrocytes using the techniques described herein.

EXAMPLE 5

Purification of MSCs from Mouse Skin

Skin from neonatal mice aged 3-15 days was dissociated and cultured in uncoated flasks containing 20 mg/mL EGF and 40 mg/mL bFGF. Over the subsequent one to five days, many (>90%) of the cells die. A small population of cells hypertrophy and proliferate to form small cell clusters growing in suspension. Some of these cells first attach to the tissue cluster plastic, hypertrophy and proliferate, and then detach as the clusters become of sufficient size. Other cells never attach to the tissue culture plastic and instead proliferate in suspension from the beginning. After four to five days, the cell clusters are small but easily distinguishable as clusters of non-adherent, proliferating cells. By seven to ten days, many of the cell clusters reach diameters of as much as 100 μm, while by two weeks, the cell clusters are macroscopic if left unperturbed. Many cells adhered to the plastic, and many died, but by about three to seven days, suspended, non-adherent clusters of up to about 20 cells formed. These suspended or floating cells were transferred to a new flask seven days after initial culturing; again, many cells adhered, but the cells in the floating clusters proliferated to generate larger clusters of more than about 100 cells (FIG. 1A, top panel). These larger clusters were then isolated, dissociated and passaged. By this process of selective adhesion, substantially pure populations of floating clusters were obtained after 3 to 4 weeks. Cells that generated these clusters were relatively abundant; 1.5 to 2 cm$^2$ of abdomen skin was sufficient to generate six 25 cm$^2$ flasks of floating clusters over this period of time.

Figure 1B:
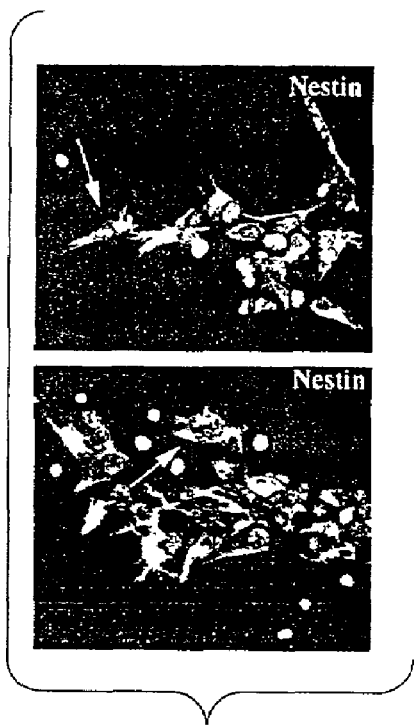

To determine whether clusters contained MSCs, we dissociated the clusters and plated the cells onto poly-D-lysine/laminin-coated dishes or chamber slides without growth factors and, 12 to 24 hours later, immunostained them for the presence of the neural precursor-specific marker nestin. After three passages, the majority of the cells expressed nestin (FIG. 1B, top panel), a property they maintained over subsequent passages. They did not, however, express the p75 neurotrophin receptor, a marker for neural crest stem cells, as detected either by immunocytochemistry or western blots. Additionally, they are negative, as detected by immunocytochemistry, for two proteins characteristic of mesenchymal stem cells: vimentin and cytokeratin.

We also determined whether the skin-derived MSCs expressed fibronectin. Four lines of skin-derived MSCs cultured from either adult (FIG. 2; left two columns) or neonatal (right two columns) mouse skin, cultured for either long term (first and third columns) or short term (second and fourth columns) were each dissociated, plated for two days in DMEM/F12 (3:1) containing 2% B-27 supplement, and then immunostained for nestin and fibronectin. As is demonstrated in FIG. 2, the majority of cells expressed both markers.

Figure 2:
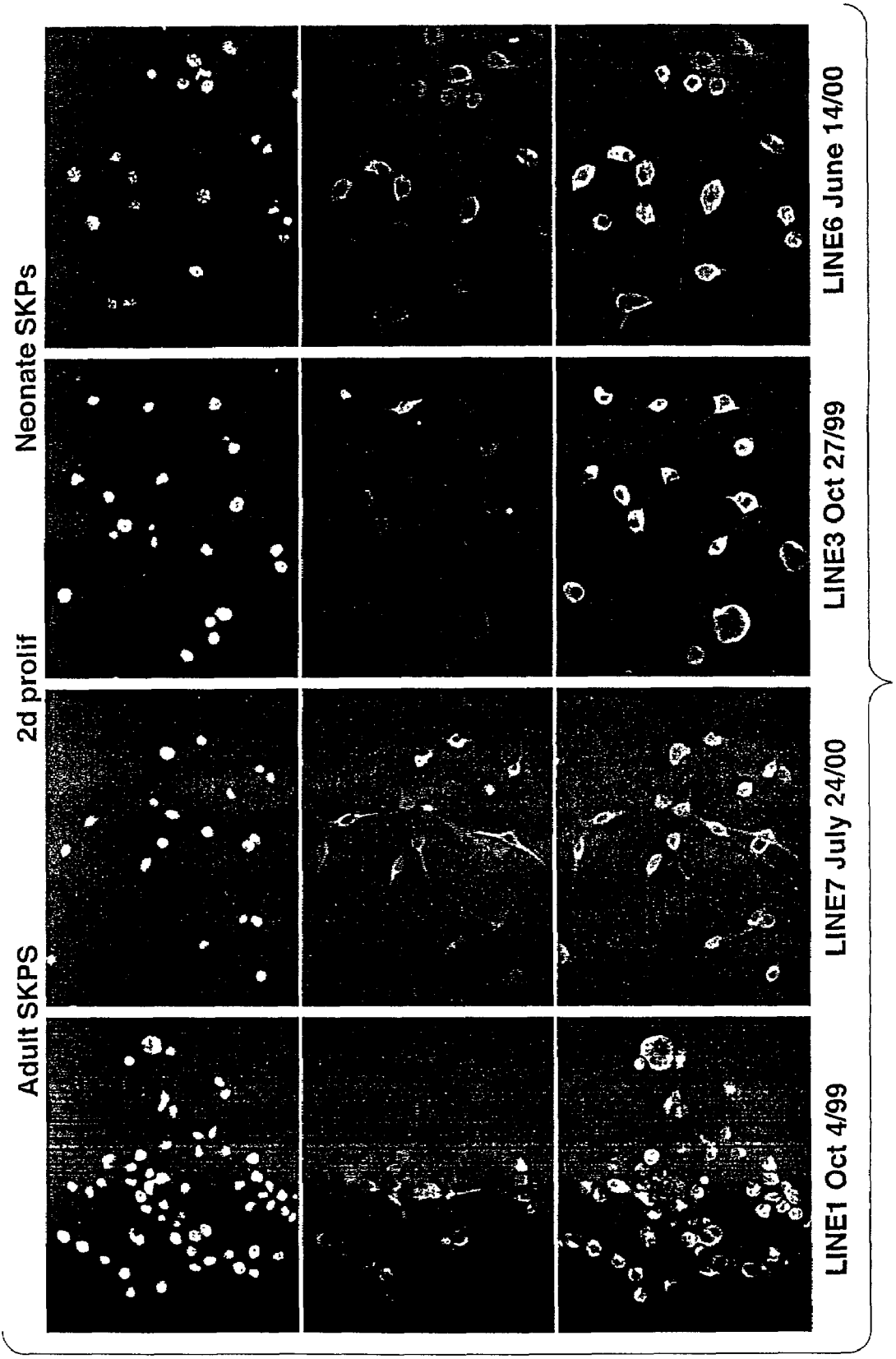
FIG. 2 is a series of photographs showing that neonate and adult mouse skin-derived MSCs express both nestin (middle row) and fibronectin protein (bottom row).

To determine whether clusters of cells could be generated from adults, skin of adult mice was dissociated and cultured as described above. Similar to neonatal mouse skin, most cells adhered to the flask or died when first cultured. After three to seven days, however, clusters of up to approximately 20 cells were observed that subsequently increased in size. When these cells were passaged at least three times (FIG. 1A, bottom panel), and plated onto poly-D-lysine/laminin overnight in the absence of growth factors, they too were immunopositive for nestin (FIG. 1B, bottom panel) and fibronectin (FIG. 2). The nestin-positive cells from adults and neonates have been passaged in this manner for over 30 passages, during which time the number would have theoretically expanded at least 10$^9$-fold (assuming a doubling time of approximately one week).

Figure 1C:
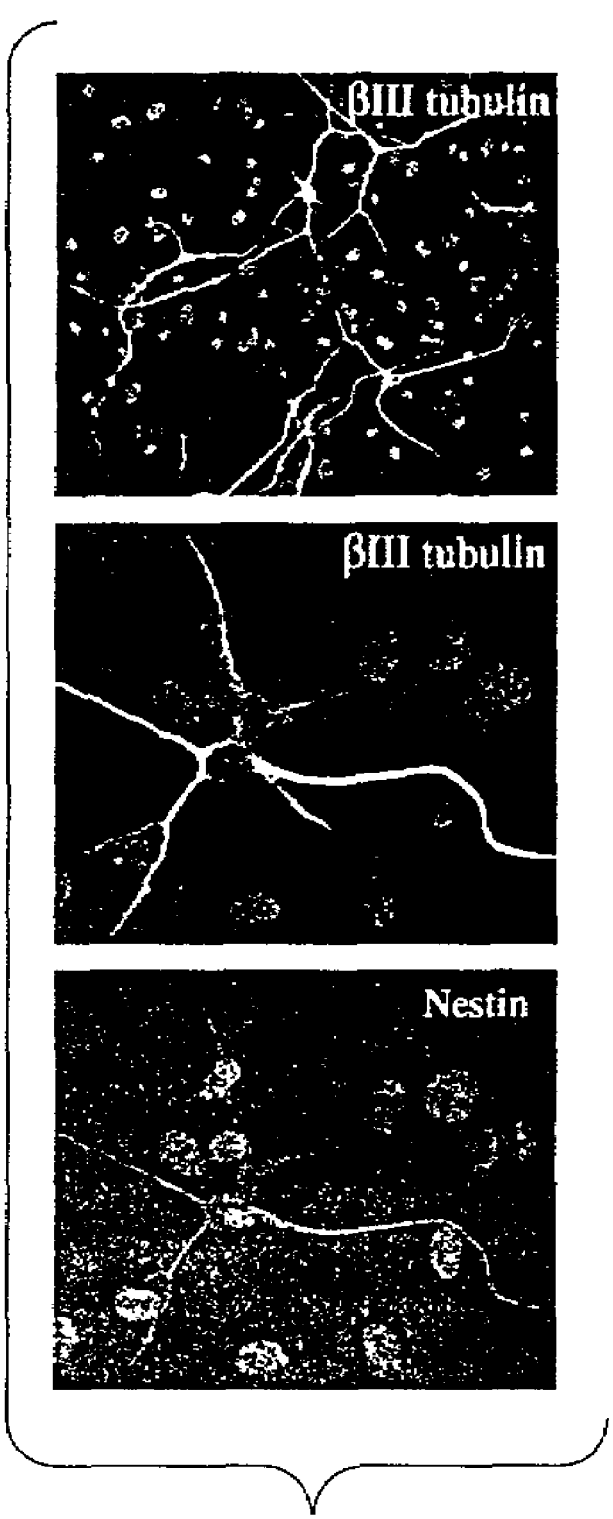
Figure 1D:
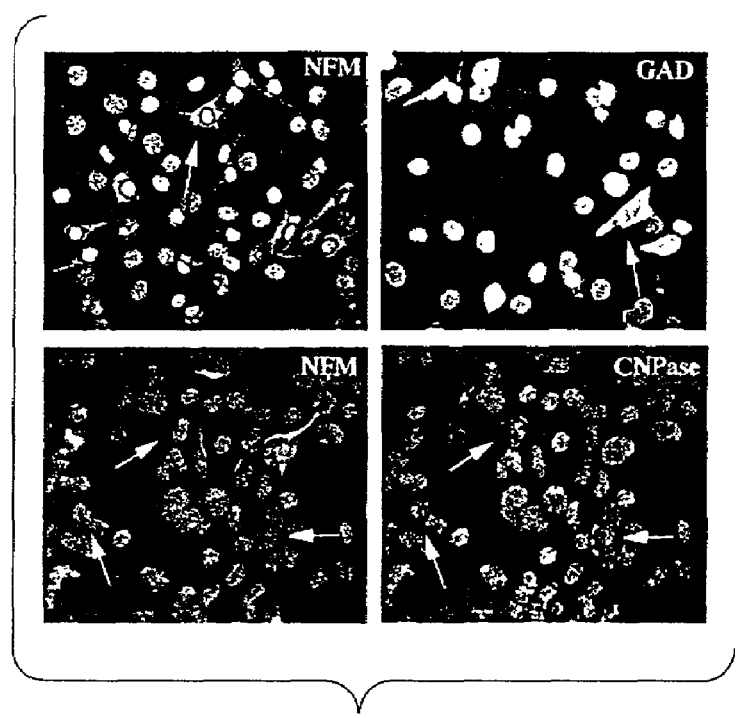
Figure 3A:
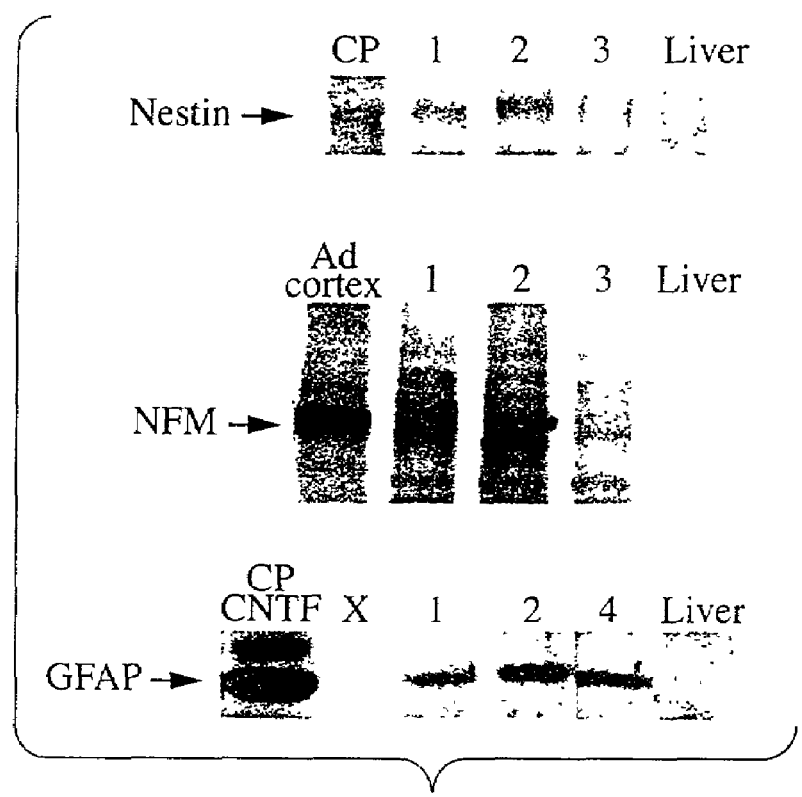
FIG. 3A is a series of photographs showing western blot analysis for nestin, neurofilament M (NF-M) and GFAP in cells differentiated from neonate and adult mouse skin-derived MSCs.
Figure 3B:
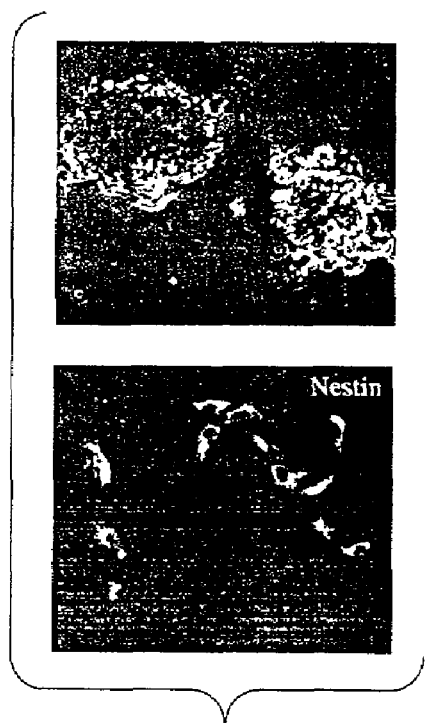
FIG. 3B is a series of photographs showing that human skin-derived MSCs express nestin.
Figure 3C:
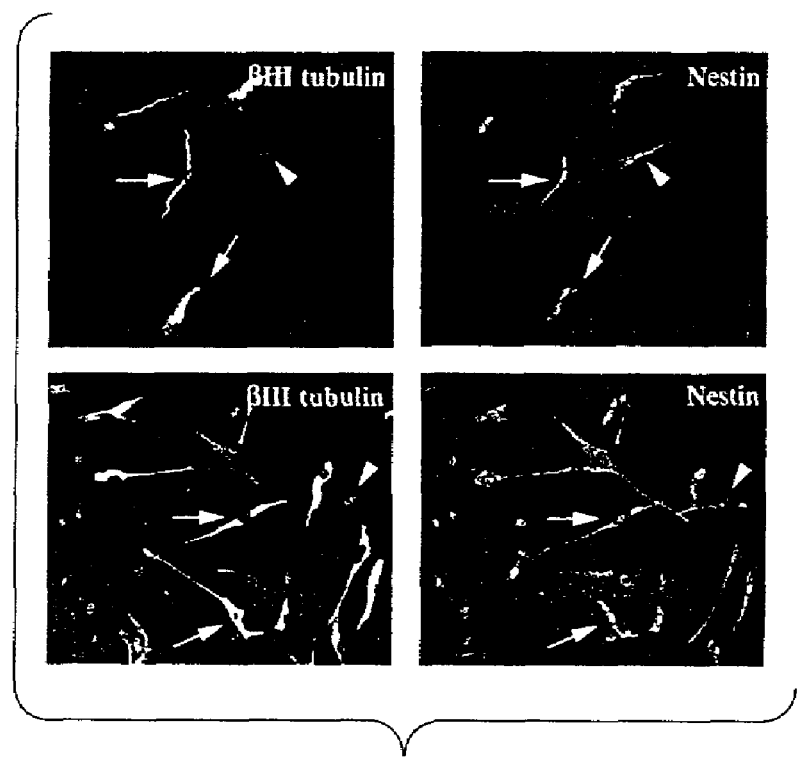
FIG. 3C is a series of photographs showing that a subset of morphologically complex cells expressed nestin and βtubulin, a profile typical of newly-born neurons.

To determine whether these nestin-positive, fibronectin-positive cells from skin could generate neural cell types, we analyzed neonatal skin-derived cells after three or more passages and greater by plating them on poly-D-lysine/laminin in the absence of growth factors. Immunostaining (FIGS. 1C and 1D) and western blot analysis (FIG. 3A) revealed that the skin-derived cells expressed neuronal markers. At seven days, a subpopulation of morphologically-complex cells coexpressed nestin and neuron-specific βIII-tubulin, a profile typical of newly-born neurons (FIG. 1C). At later time points of 7-21 days, cells also expressed neurofilament-M (NF-M) (FIGS. 1D, 3A), neuron-specific enolase, and NeuN, three other neuron-specific proteins. Finally, some neurofilament-positive cells expressed GAD (FIG. 1D), a marker for GABAergic neurons, which are not found in the PNS. Similar results were obtained for adult skin-derived MSCs, although at early passages some of the βIII-tubulin and neurofilament-positive cells were less typically neuronal in morphology.

Figure 1E:
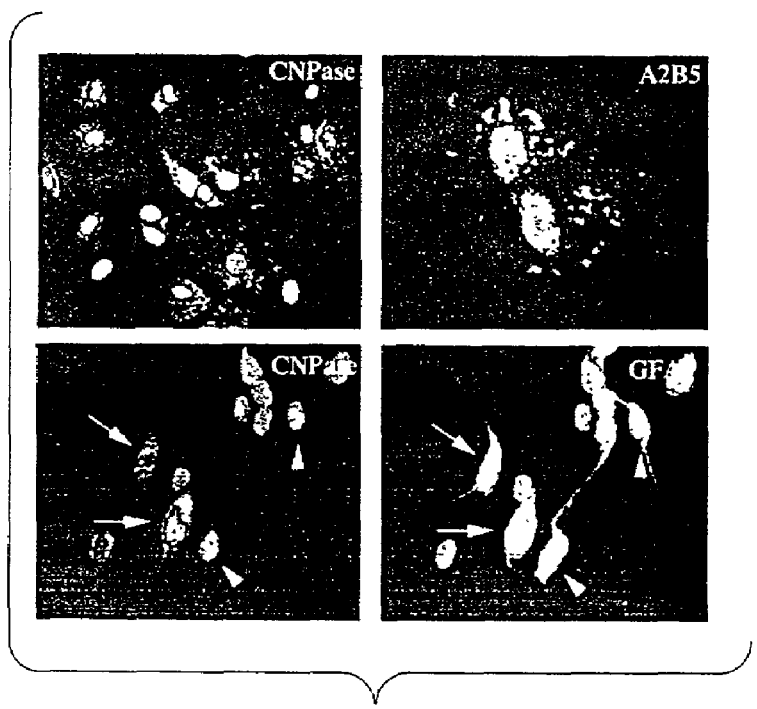
Figure 1F:
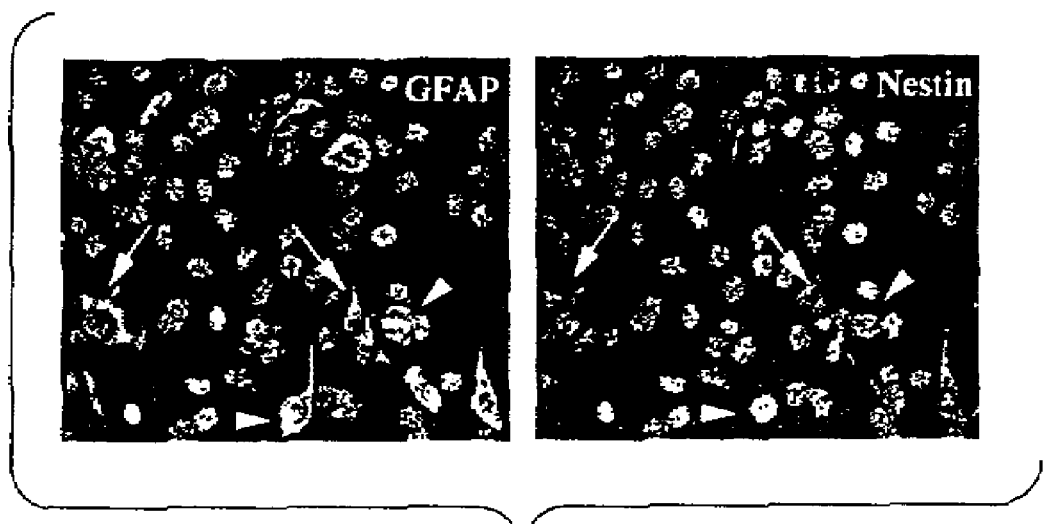
Figure 4A:
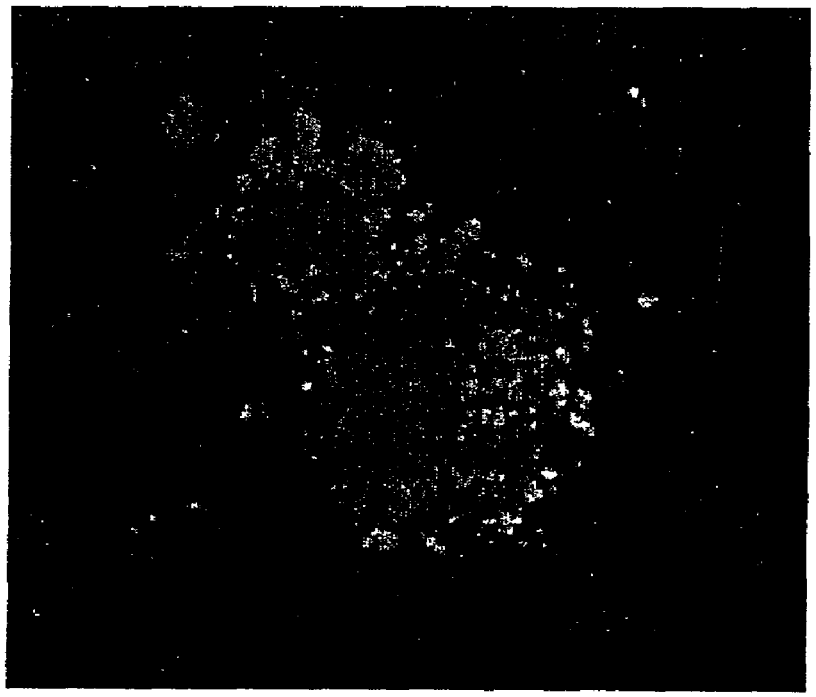
FIG. 4A is a photograph showing the expression of A2B5, a marker for oligodendrocyte precursors, on undifferentiated mouse skin-derived MSCs.
Figure 4B:
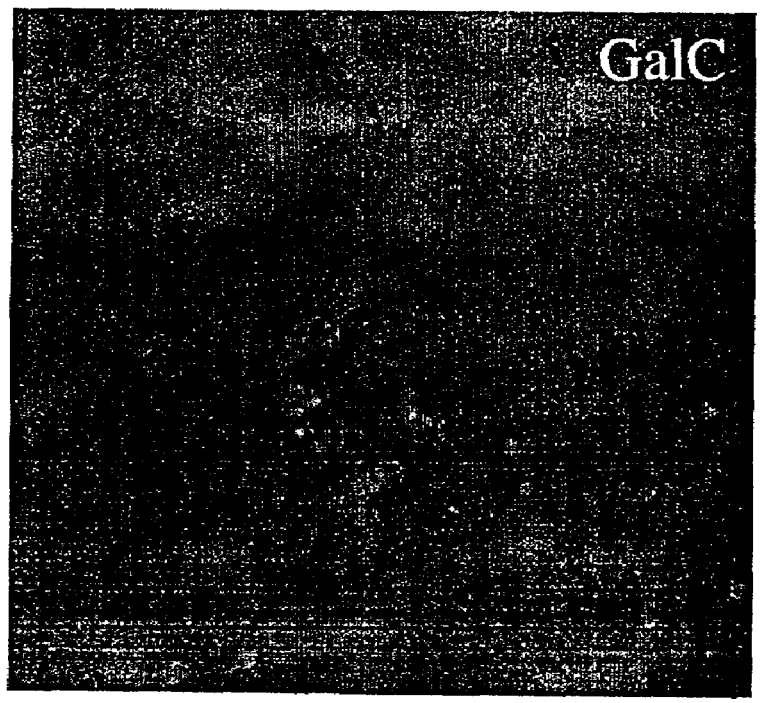
FIG. 4B is a photograph showing the expression of the oligodendrocyte marker galactocerebroside (GalC) on cells differentiated from mouse skin-derived MSCs.

Immunostaining and western blots revealed that both neonatal and adult MSCs generated cells expressing the glial markers GFAP and CNPase at seven to twenty-one days after plating (FIGS. 1D-1F, 2A). Double-labeling for these proteins demonstrated the presence of (i) cells that were GFAP-positive but not CNPase-positive (potentially astrocytes), (ii) cells that expressed CNPase but not GFAP (potentially oligodendrocytes or their precursors), and (iii) a small subpopulation that were bipolar and expressed both CNPase and GFAP (potentially Schwann cells) (FIG. 1E). A subpopulation of GFAP-positive cells also expressed nestin, a finding previously reported for developing CNS astrocytes. Additionally, some cells were positive for A2B5, a marker for oligodendrocyte precursors (FIG. 4). Like GAD-positive neurons, astrocytes and oligodendrocytes are normally found only in the CNS.

Figure 1G:

Double-labeling studies supported the following additional conclusions. First, glial versus neuronal markers were expressed in distinct subpopulations of MSCs progeny. Second, after twenty passages, skin-derive MSCs were still able to differentiate into neurons and glial cells. Finally, skin-derived MSCs were able to generate smooth muscle cells (as determined by both expression of smooth muscle actin (SMA) and morphology; FIG. 1G), adipocytes (FIGS. 5 and 6), cartilage, bone, cardiac muscle, and skeletal muscle.

EXAMPLE 6

MSCs Originate from the Dermal Layer of the Skin

Figure 7A:
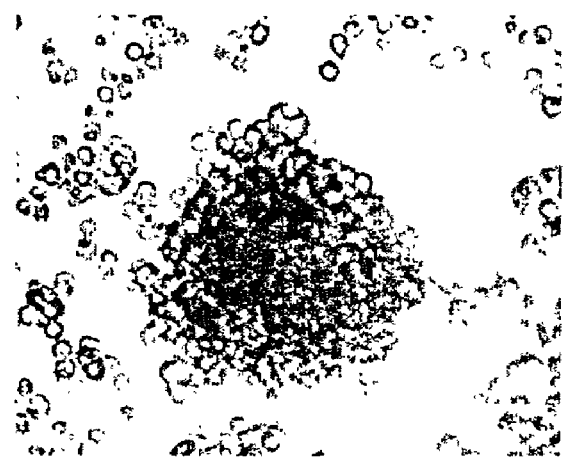
FIGS. 7A and 7B are photographs showing that nestin-positive, fibronectin-positive MSCs can be derived from mouse dermis.
Figure 7B:
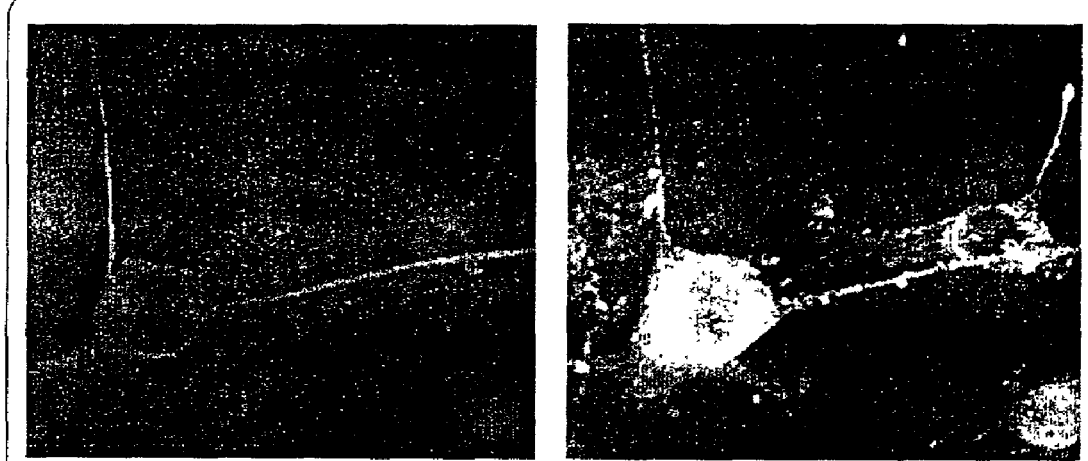

The two major layers of the skin are the epidermis and the dermis. To determine the origin of the skin-derived MSCs, we dissected and cultured P7, P14, and P18 mouse epidermis and dermis. The two layers of the skin were separated by incubating the skin pieces (1×2 cm$^2$) in 0.2% trypsin at 40° C. for about 24-36 hours, or until the dermis could be separated from the epidermis. The cells in each layer were dissociated separately and then cultured in DMEM/F12 (3:1) with B-27 supplement, EGF (20 ng/mL) and FGF (40 ng/mL). Only the cells derived from the dermis generated clusters of cells similar to those derived from whole skin (FIG. 7A). No viable cells were obtained from the epidermis. To characterize the dermis-derived cell clusters, the clusters were cultured for four weeks and then plated onto tissue culture chamber slides coated with poly-D-lysine and laminin. After 24 hours, the cells were then processed for immunocytochemistry. Like MSCs derived from whole mouse skin, the dermis-derived cells coexpressed nestin and fibronectin (FIG. 7B).

EXAMPLE 7

Clonal Analysis Indicates that Skin-Derived MSCs are Multipotent

Figure 8B:
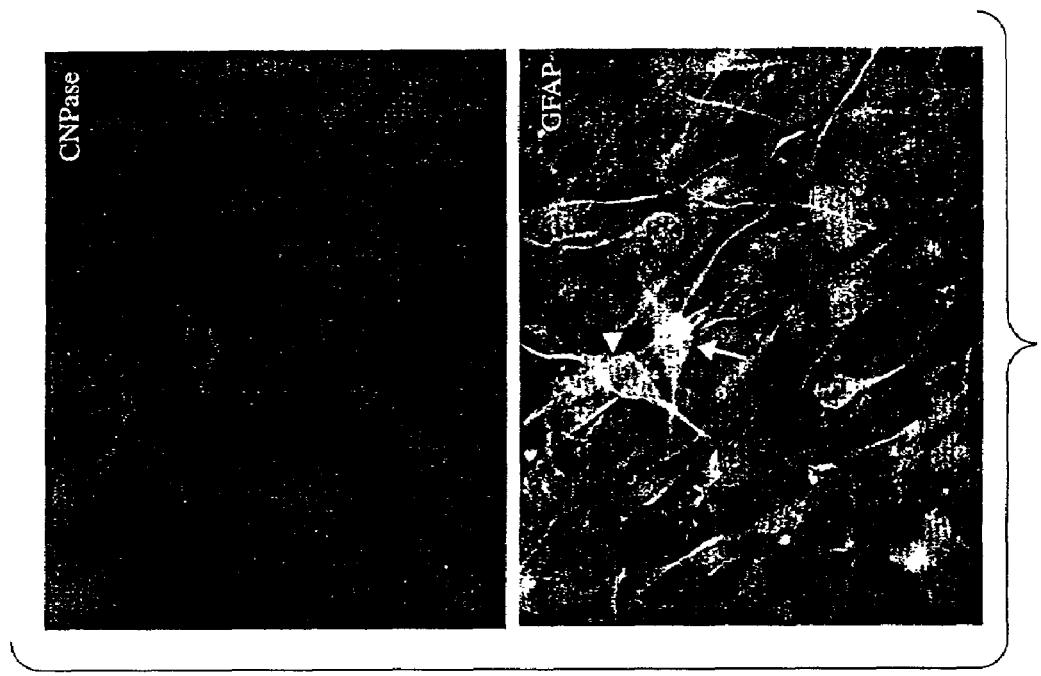
FIGS. 8A and 8B are photographs showing that individual MSCs are multipotent. Clones derived from single cells contained NF-M-positive cells (arrowheads) and CNPase-positive cells (arrows). Arrowheads indicate cells that only express GFAP, while arrows indicate cells expressing both GFAP and CNPase.
Figure 8A:
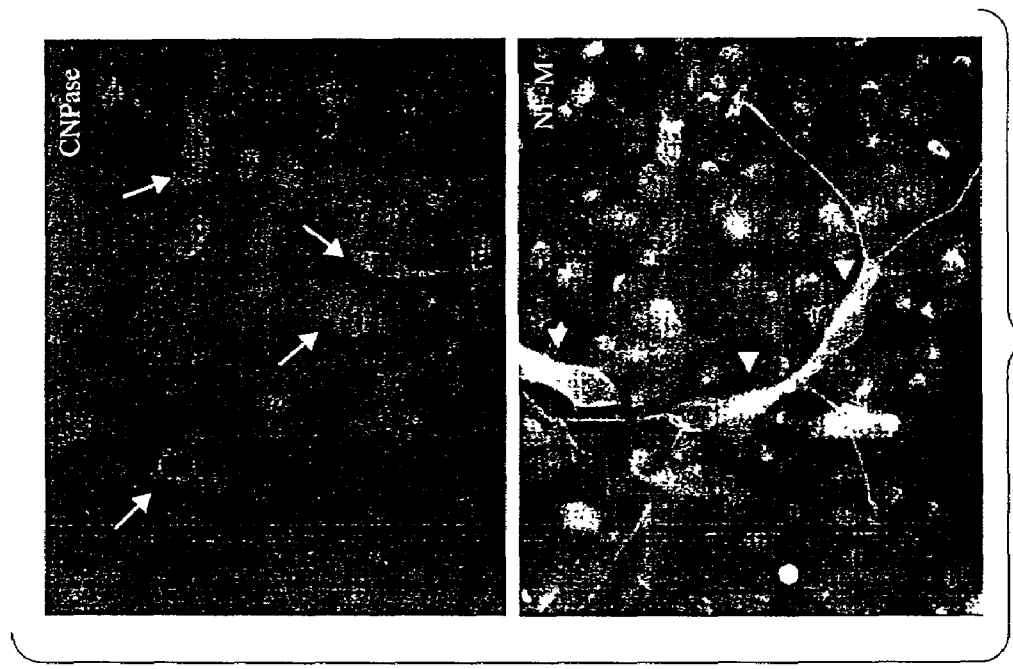

To determine whether skin-derived MSCs are multipotent, we isolated single cells by limiting dilution of cells from clusters that three months prior had been derived from neonatal mice. We cultured the cells for five weeks in medium from the same culture line and containing growth factor, and then differentiated the cells for two weeks in medium lacking growth factor but containing 3% rat serum. The cells were then processed for immunocytochemistry. As is demonstrated in FIG. 8, single clones of cells contained NF-M-and CNPase-positive cells (FIG. 8A), and GFAP- and CNPase-positive cells (FIG. 8B).

EXAMPLE 8

Western Blot Analysis of Skin-Derived MSCs

Figure 9A:
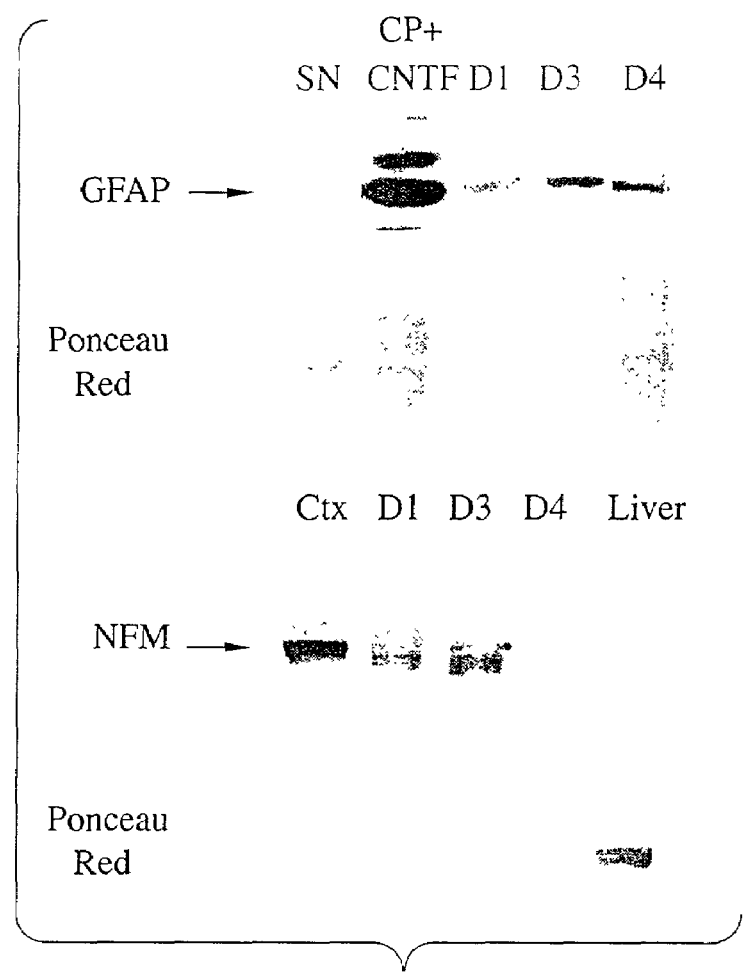
FIGS. 9A and 9B are photographs of western blot analysis of cells differentiated from mouse skin-derived MSCs (FIG. 9A) or of MSCs themselves (FIG. 9B).
Figure 9B:
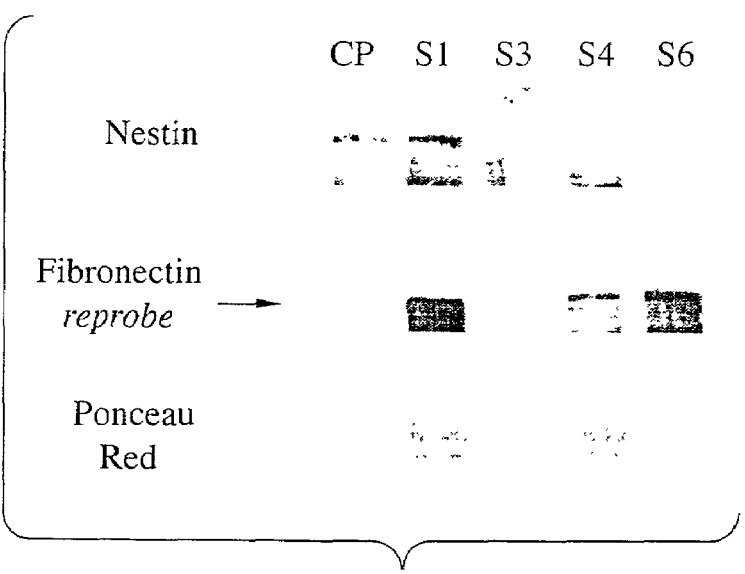

For western blot analysis of skin-derived MSCs, four cultures (one adult-derived line and three neonate-derived lines) that had been passaged from seven to 40 times were analyzed either as clusters or following differentiation by plating in medium containing 1% FBS, B-27 supplement, and fungizone for 14 days in 60 mm dishes coated with poly-D-lysine and laminin. Cell lysates were prepared, and equal amounts (50-100 µg) of protein from each culture were separated on 7.5% or 10% polyacrylamide gels, transferred to membrane, and then probed with anti-nestin monoclonal antibody (1:1000; Chemicon), anti NF-M polyclonal antibody (1:1000; Sigma), anti GFAP polyclonal antibody (1:1000, Dako), or anti fibronectin polyclonal antibody (1:1000; Sigma). As positive controls, we used cortical progenitor cells cultured in the presence of CNTF (which results in astrocytic differentiation) or in the absence of CNTF (which results in neuronal differentiation) and adult mouse cortex. As negative controls, we used sympathetic neurons and liver. As illustrated in FIG. 9A, western blotting confirmed the expression of GFAP and NF-M in cultures differentiated from both adult and neonate skin-derived MSCs. Similarly, FIG. 9B illustrates the expression of both nestin and fibronectin in adult and neonate skin-derived MSC clusters.

EXAMPLE 9

MSC Differentiation can be Modulated by Plating Conditions

Figure 5:
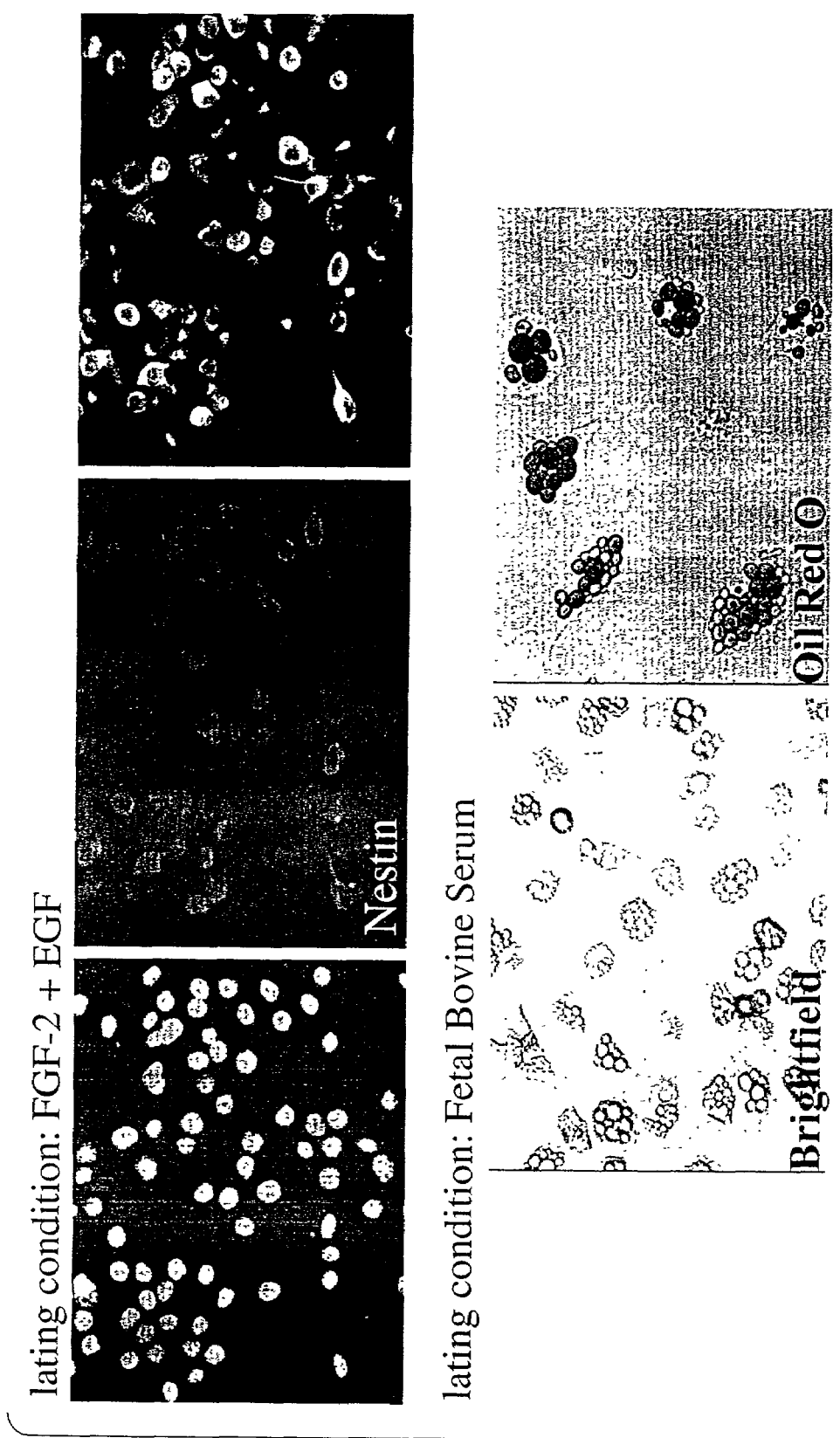
FIG. 5 is a series of photographs showing that the fate of mouse skin-derived MSCs can be manipulated by controlling plating conditions.
Figure 6:
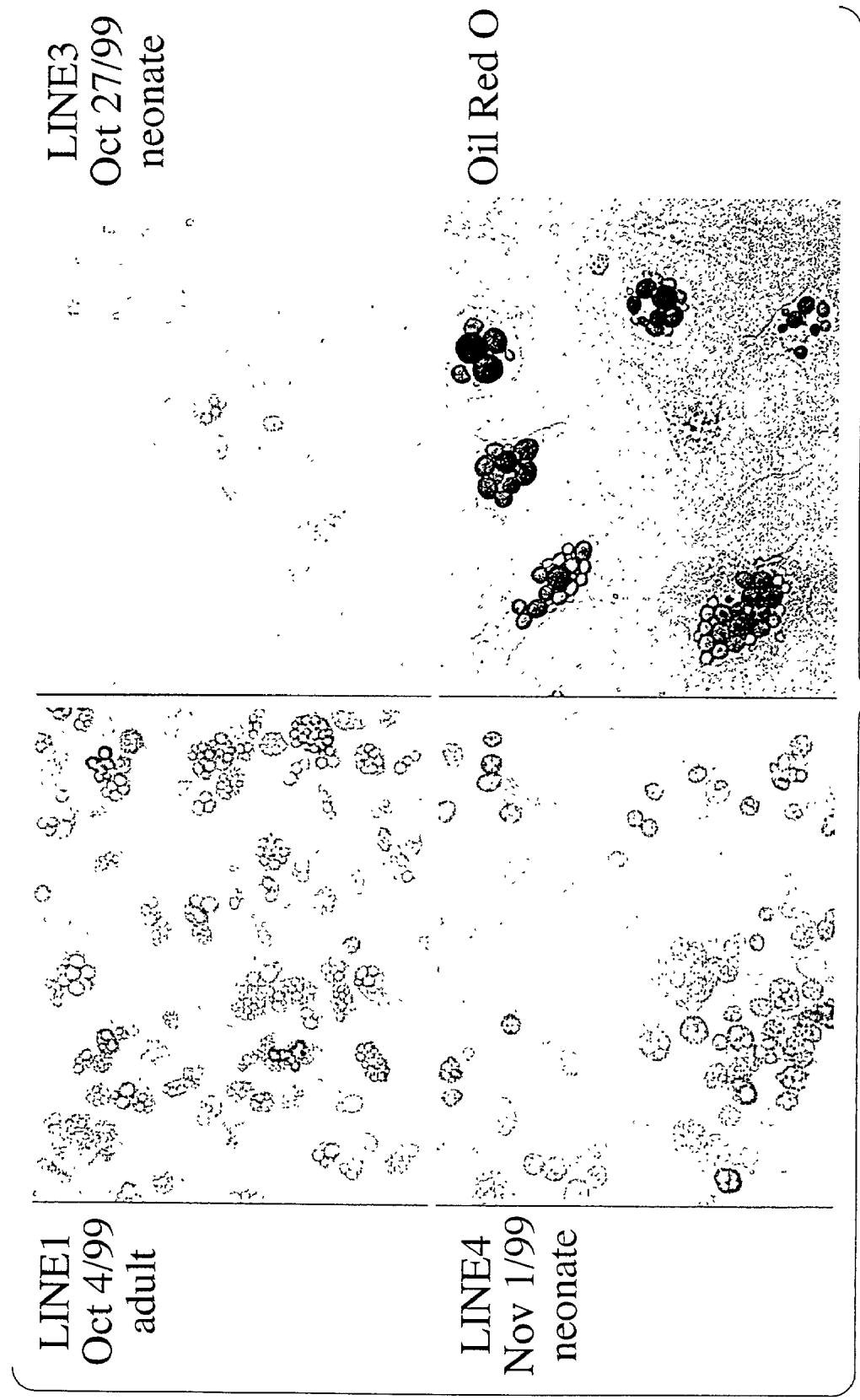
FIG. 6 is a series of photographs showing that neonate and adult mouse skin-derived MSCs can differentiate as adipocytes.

As is illustrated above, when clusters of skin-derived MSCs are dissociated and plated in medium containing FGF and EGF, most of the nestin-positive cells become neurofilament-positive. We have found that when the cells are plated in medium containing 10% FBS, the cells adopt a morphology similar to that displayed by adipocytes. The adoption of the adipocyte cell fate was confirmed by staining with Oil Red O (FIG. 5). The ability of 10% FBS to induce adipocyte differentiation was true for both adult and neonate skin-derived MSCs (FIG. 6).

This example demonstrates both the ability of skin-derived MSCs to differentiate to mesodermal cell types, and the significant effects of plating conditions on the proliferation, differentiation and survival of skin-derived MSCs. In addition to serum concentration, other plating conditions can be altered to influence the proliferation, differentiation, and survival of these cells. Such plating conditions include plating density, the addition of pharmacological agents to the culture media (i.e., pharmacological inhibitors,), the addition of therapeutic protein(s) to the culture media (i.e., growth factors, cytokines, anti-apoptotic proteins), and the addition of small molecules that agonize or antagonize the function of a protein(s) and/or modulate signaling through a signal transduction pathway important in regulating the proliferation, differentiation, or survival of the skin-derived MSCs. These parameters can be altered individually, or in combination to influence the proliferation, differentiation or survival of the skin-derived MSCs. For example, one or more therapeutic proteins can be added to the culture media Furthermore, therapeutic proteins can be added in combination with changes in plating density. Still another embodiment combines the addition of therapeutic protein(s) with the addition of a small molecule. Additional plating conditions include the co-culture of the skin-derived MSCs with other cells or cell types, and the pre-sorting of the skin-derived MSCs prior to plating.

Examples of the effects of altering several different plating conditions are presented below.

EXAMPLE 10

Figure 10:
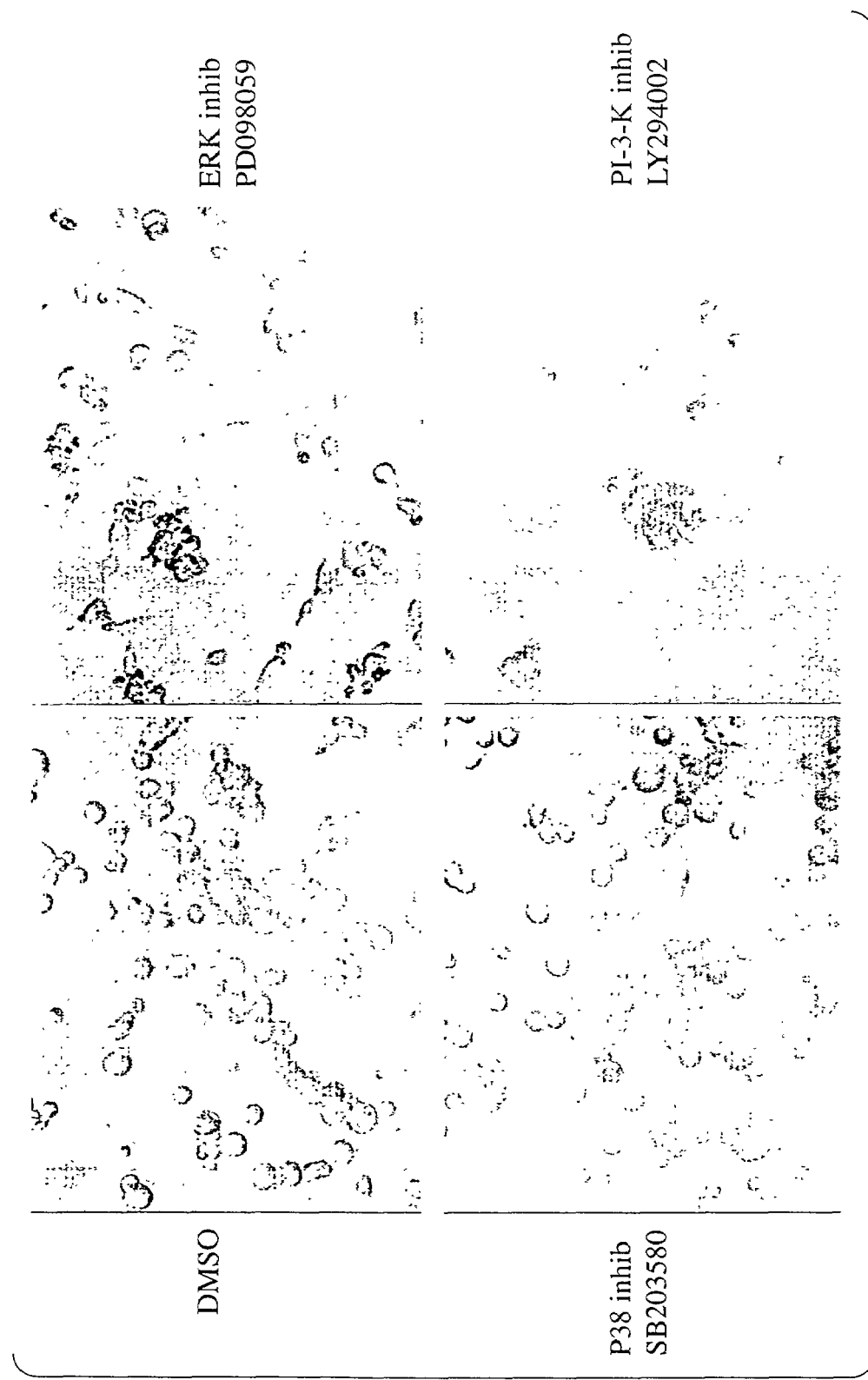
FIG. 10 is a series of photographs showing the effect of various pharmacological agents on mouse skin-derived MSCs.

Pharmacological inhibitors affect survival and proliferation of skin-derived MSCs When skin-derived MSCs are plated for three days in proliferation medium containing FGF, they typically exhibit a spherical morphology characteristic of their proliferative state (FIG. 10). We tested the ability of pharmacological agents to alter this phenotype. Supplementing the medium with PD098059 (an inhibitor of the ERK MAPK pathway) caused proliferating cells to flatten and differentiate (FIG. 10), while supplementing with LY294002 (an inhibitor of the PI-3-K pathway), caused the cells to die (FIG. 10). The p38 MAPK inhibitor SB203580 had no observed effect on the proliferating skin-derived MSCs.

These and other pharmacological agents could be added to the culture media to influence cell proliferation, differentiation, and survival. Pharmacological agents can be added alone or in combination, and combinations of agents can be co-administered or administered at different times. Additionally, pharmacological agents can be administered in combination with one or more therapeutic proteins or small molecules to influence cell proliferation, differentiation, and survival. Such combinations of pharmacological agents and therapeutic proteins can be co-administered or administered at different times to influence cell proliferation, differentiation, and survival.

EXAMPLE 11

Purification of Nestin-Positive Cells from Adult Human Skin

We have purified nestin-positive cells from human scalp. To purify MSCs from human skin, we utilized tags of scalp tissue generated by placement of a stereotactic apparatus during neurosurgery. Scalp tags totalling 1 $cm^2$ or less from each of eight individuals were used. The skin included dermal and epidermal tissue. Tissue was cut into smaller pieces that were then transferred into HBSS containing 0.1% trypsin for forty minutes at 37° C. Following trypsinization, tissue samples were washed twice with HBSS and once with DMEM:F12 (3:1) supplemented with 10% rat serum to inactivate the trypsin. Trypsinized tissue was then mechanically dissociated by trituration in a pipette and the resulting dispersed cell suspension was poured through a 40 µm cell strainer into a 15 mL tube. The tube was then centrifuged for five minutes at 1000 rpm (~1200×g). The cells were resuspended in DMEM:F12 medium containing 40 ng/mL bFGF, 20 ng/mL EGF, 2% B-27 supplement, and antibacterial and antifungal agents, and then cultured in 12 well plastic tissue culture plates. Every seven days, the cell clusters are harvested by centrifugation, triturated with a fire-polished pasteur pipette, and cultured in fresh medium.

As for the use of rodent skin, most cells (>75%) adhered to the plastic or died, but after seven days, small floating clusters of cells were observed. These clusters were then partially dissociated and transferred to new wells, where they slowly increased in size. After additional passaging, clusters were plated on poly-D-lysine/laminin in 3% FBS with no growth factors, and analyzed for the presence of neural markers.

Within two weeks, greater than 30% of the cells within the cell clusters were nestinpositive. Immunolabeling of four to six week old cultures also revealed that many of the cells in the clusters were nestin-positive with the percentage varying from less than 50% to greater than 80% two to three days after plating, and that greater than 70% of the cells were fibronectin positive. Double-label immunocytochemistry at the same or longer time-points revealed that, in all cultures, some nestin-positive cells also expressed βIII-tubulin and displayed elongated neurites. Thus, adult human skin is a source for nestin-positive and fibronectin positive MSCs cells that, when differentiated, can express neuron-specific proteins.

EXAMPLE 12

Purification and Differentiation of MSCs Derived from other Human Peripheral Tissues Containing Sensory Receptors MSCs can be purified from human olfactory epithelium using the same procedures as described for the purification of stem cells from rodent olfactory epithelium. Source material is acquired by surgical removal of olfactory epithelial tissue from the donor. Because the MSCs are capable of proliferation and self-renewal, little source tissue is required. Preferably, the amount is at least about 1 mm$^3$. Conditions for culturing human cells are described in Example 11, above. Other conditions are known to those skilled in the art, and can be optimized for proliferation or differentiation of neural stem cells, if desired.

We can purify MSCs from other peripheral tissues containing sensory receptors, other than the olfactory epithelium, tongue, and skin, using techniques described herein. Passaging and differentiation of these cells is also performed using the same techniques described herein. Other peripheral tissues containing sensory receptors include, for example, mucosal membranes from the mouth or reproductive system.

EXAMPLE 13

Transformation of MSCs

In therapy for neurodegenerative diseases, it may be desirable to transplant cells that are genetically modified to survive the insults that caused the original neurons to die. In addition, MSCs may be used to deliver therapeutic proteins into the brain of patients with neurodegenerative disorders to prevent death of host cells. Exemplary therapeutic proteins are described herein. In still another example, MSCs can be induced to differentiate into a desired cell type by transfecting the cells with nucleic acid molecules encoding proteins that regulate cell fate decisions (e.g., transcription factors such as Isl-1, en-1, en-2 and nurr-1, implicated in regulating motor-neuron and striatal phenotypes). Using such a method, it is possible to induce the differentiation of the specific cell types required for transplant therapy. Therefore, it would be advantageous to transfect MSCs with nucleic acid molecules encoding desired proteins. We have previously used recombinant adenovirus to manipulate both postmitotic sympathetic neurons and cortical progenitor cells, with no cytotoxic effects. We now have established that olfactory epithelial-derived MSCs and skin-derived MSCs can each be successfully transfected with high efficiency and low toxicity. MSCs can be transfected either transiently or stably using not only adenoviral mediated methods, but also using lipofectamine or electroporation.

EXAMPLE 14

Differentiation of MSCs into the Appropriate Cell Type in vivo Following Transplantion into Adult Rodent Brain One therapeutic use for the MSCs of the present invention is autologous transplantation into the injured or degenerating CNS or PNS to replace lost cell types and/or to express therapeutic molecules. We demonstrate below that the MSCs can differentiate into neurons when transplanted into the adult brain.

If desired, the dopaminergic innervation of the adult striatum can be unilaterally destroyed by a local infusion of 6-hydroxydopamine under conditions in which noradrenergic neurons are spared. Several weeks later, MSCs are transplanted into both the intact and lesioned striatum. Altenatively, the cells can be transplanted into unlesioned animals. The fate of the transplanted MSCs is then determined by immunohistochemistry. Exemplary transplantation studies are described below. These studies demonstrate that transplanted MSCs can differentiate into neurons in vivo, as they can in vitro. In the former case, differentiation and cell fate choice is controlled by the local environment into which each cell is placed. Both in vitro-differentiated and undifferentiated cells are useful therapeutically in the treatment, for example, of neurodegenerative disease (e.g., Parkinson's disease and multiple sclerosis) or spinal cord injury. For example, dopamingeric neurons differentiated from MSCs, or the MSCs themselves, may be transplanted into the substantia nigra or the striatum of patients having Parkinson's disease. If desired, the MSCs may also be genetically-modified to express a desired protein. Such genetic modification may help influence the proliferation, differentiation, and survival of the MSCs. In one embodiment, the genetic modification protects the transplanted cells from the conditions which caused the degeneration of the endogenous cells.

In one example, the dopaminergic innervation to adult rat striatum was first unilaterally lesioned with the chemotoxin 6-hydroxydopamine, and the efficacy of the lesions was tested two weeks later by amphetamine-induced rotational behavior. Two days prior to transplantation, rats were immunosuppressed with cyclosporin. MSCs, produced from olfactory epithelia as described herein, were then stereotactically injected into the caudate-putamen complex on both the lesioned and unlesioned sides. Sixteen days following transplantation, animals were sacrificed, and sections of the striatum were analyzed for nestin- and TH-immunoreactivity. Five of eight animals received successful injections of MSCs in the striatum. Of these, four animals showed evidence of a nestin-positive tract on both the lesioned and unlesioned sides, although tracts on the lesioned side appeared to be more intensely nestin-immunoreactive. On adjacent sections, TH-positive cells were observed confined to an area close to the transplant tract on both the lesioned and unlesioned side. As many as 25-30 TH-positive cells were identified on each section. Cell morphology varied from small, round cells lacking processes to neurons that were morphologically complex with multiple fine processes. In some cases, the processes of these TH-positive neurons extended into the striatum for distances of up to 300 μm.

To confirm that these TH-positive neurons derived from the MSCs, we performed two sets of experiments in which the transplanted cells were detectably-labeled. In one set of experiments, transplanted MSCs were derived from T 1:nlacZ transgenic mice, in which the neuron-specific T 1 α-tubulin promoter drives expression of a nuclear-localized β-galactosidase marker gene. Immunohistochemical analysis of animals receiving the transgenic MSCs revealed the presence of β-galactosidase-positive neurons within the transplant tract, confirming that the transplanted MSCs generated neurons in vivo, as they did in vitro. In a second set of experiments, MSCs were labelled with BrdU for 18 hours, washed to remove the BrdU label, and then transplanted unilaterally into the 6-hydroxydopamine-lesioned striatum of animals (10 rats, 4 mice) prepared as described herein. Immunohistochemical analysis with an anti-BrdU antibody revealed that all animals showed evidence of BrdU-positive transplant tracts. Immunocytochemistry with anti-GFAP revealed that, in both xenografts and allografts, GFAP-positive cells with heterogeneous morphology were concentrated at the transplant site, but were also present in moderate amounts over the entire ipsilateral hemisphere, with additional scattered reactive astrocytes seen in the contralateral hemisphere. GFAP-BrdU double-labelled cells were present mainly within or close to the transplant tract, and varied in morphology from small, round cells with only a few processes, to large polygonal or fusiform cells with multiple processes. Immunohistochemistry with anti-TH revealed that TH-BrdU double-labeled cells were also present, although these were few in number relative to GFAP-BrdU positive cells. BrdU-TH double-labeled cells were mainly small to medium-sized without processes, although some examples of double-labeled cells with processes were found within and adjacent to, the transplant tract. Thus, MSCs generated astrocytes and neurons in vivo, and a subpopulation of the latter were TH-positive. Together, these findings show that peripheral tissue-derived MSCs are capable of generating cell types that are never found within olfactory tissue, including oligodendrocytes and TH-positive neurons.

Figure 3D:
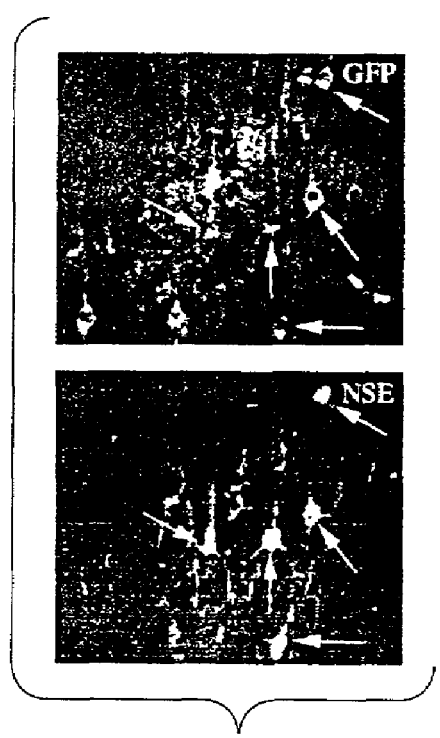
FIG. 3D is a series of photographs showing that GFP positive cells are also positive for neuron-specific enolase.
Figure 11A:
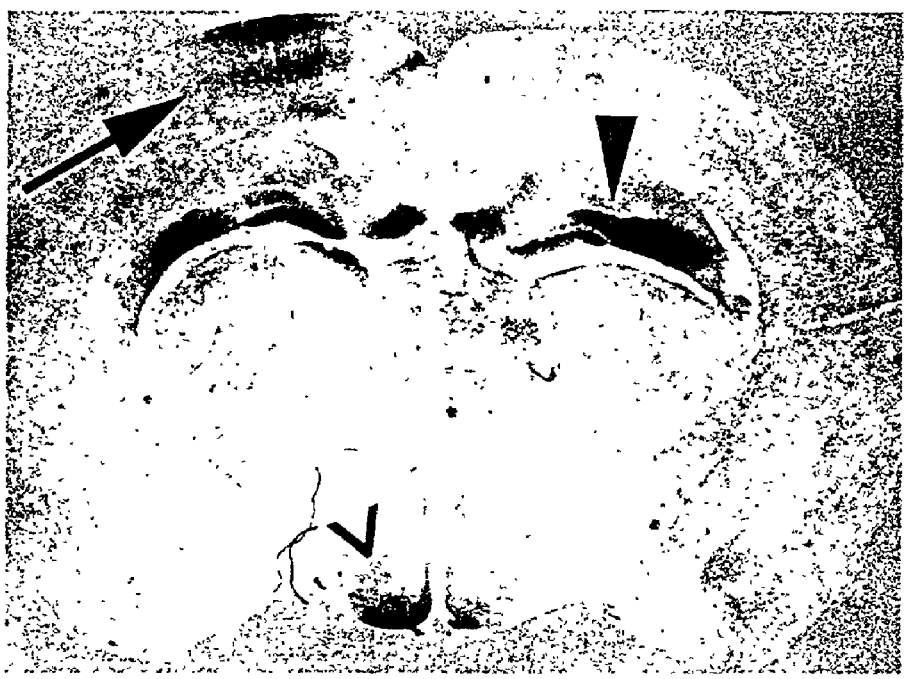
FIGS. 11A-11E are photographs of immunoprocessed sections of rat brains into which mouse skin-derived MSCs were transplanted.
Figure 11B:
Figure 11C:
Figure 11D:
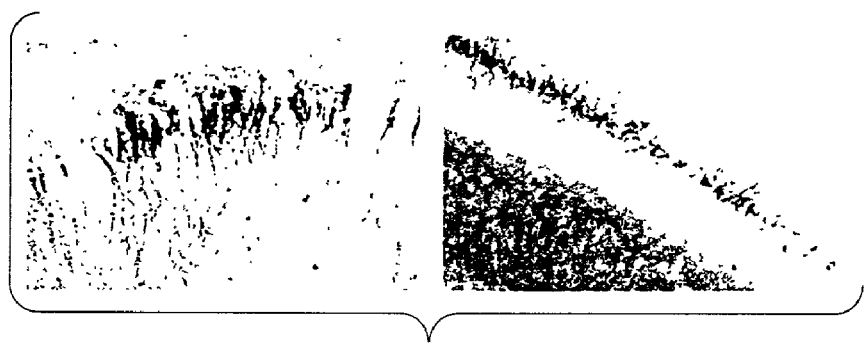

To determine whether skin-derived MSCs also generate differentiated neural cell types in vivo, we tagged adult mouse skin-derived MSCs with (i) BrdU, and (ii) a recombinant adenovirus expressing GFP, and then transplanted them as cell clusters of about 20 to about 100 cells into the lateral ventricles of P2 rats. Immunostaining fourteen days later revealed that, in all animals analyzed (n=8), transplanted cells had migrated extensively (FIG. 11A). In particular, tagged cells had integrated into the cortex, the hypothalamus and the amygdala in all, and into the hippocampus in two of the transplanted brains (FIG. 11A). In the cortex, GFP-positive cells were located in patches (FIGS. 11A, 11B) or occasionally as single cells (FIG. 11C), including some that had integrated into and adopted the morphology of layer V pyramidal neurons (FIGS. 11B, 11C). These cells had triangular-shaped soma, and projected a presumptive apical dendrite from layer V towards layer I, in a manner similar to the endogenous layer V neurons. That these cells were neurons was demonstrated by double-labeling for neuron-specific enolase (FIG. 3D). Immunocytochemical analysis also confirmed that these were transplanted cells, as BrdU-positive cells were present in the same locations as GFP-positive cells in all brains (FIG. 11B).

Figure 11E:
Figure 12A:
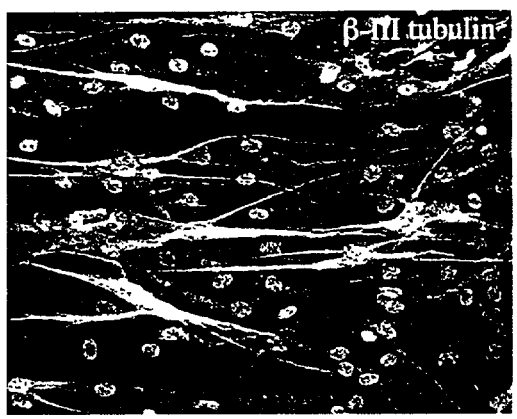
FIG. 12 shows that nestin+, fibronectin+skin-derived MSCs isolated from adult human scalp differentiate into cells that express a variety of neural and non-neural markers, as measured by immunocytochemistry with antibodies to βIII-tubulin (A), CNPase (B), and smooth muscle actin (C), and GFAP (D).
Figure 12B:
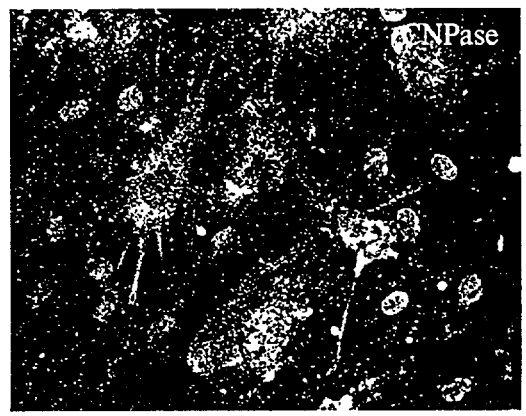
Figure 12C:
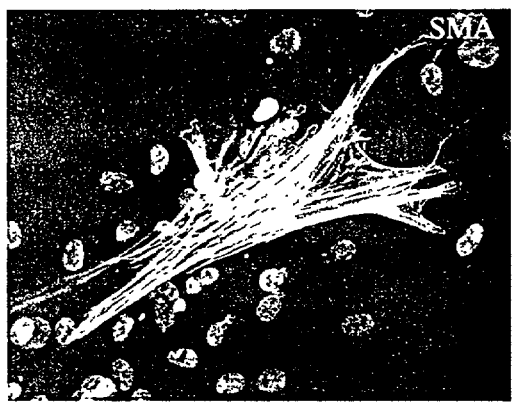
Figure 12D:
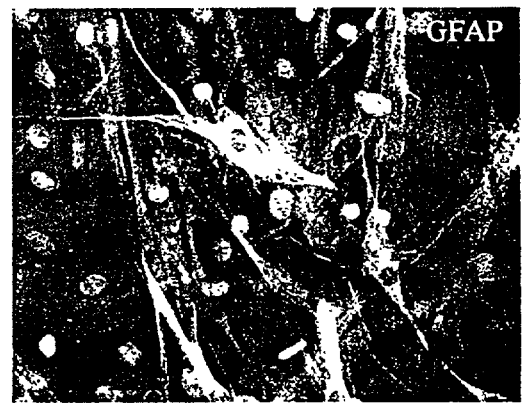

In both the amygdala and hippocampus, transplanted cells also displayed neuronal morphology. In the amygdala, GFP and BrdU-positive cells were large, with prominent nuclei, and extensive processes (FIG. 11E). In the hippocampus, transplanted cells had integrated into both the dentate gyrus and pyramidal cell layers, and their morphology was typical of the endogenous granule and pyramidal cells, respectively (FIGS. 11A, 11E). GFP-positive staining was also seen within the molecular layer. Finally, GFP- and BrdU-positive cells were observed in other locations, such as the hypothalamus, where the morphology of many cells was not typically neuronal.

Skin-derived MSCs tranplanted into adult rats also survive and integrate. We labeled adult mouse skin-derived MSCs that had been passaged more than thirty times with the nuclear dye 33258, washed extensively, and then injected the cells stereotactically into the brains of adult rats that were immunosuppressed with cyclosporin. Four weeks later, we sacrificed the animals by perfusion and processed the brains for histological examination. Hoeschst-labeled cells were present in the hippocampus, olfactory bulb, and striatum. From these data, we conclude that the transplanted skin-derived MSCs are capable of survival following transplantation. Moreover, cells are capable of migrating from the site of injection to numerous brain regions.

Skin-derived MSCs are also capable of survival, migration, and integration following transplantation into a hemisected adult mouse spinal cord. In this example, the cells were injected into the injured sides of hemisected spinal cords. Eight days later, the animals were sacrificed and the spinal cords processed for histological analysis. Hoechst-labeled cells were present at the site of the initial injection, and had also migrated extensively into the injured spinal cord.

EXAMPLE 15

Differentiation of Non-Neural Cells from MSCs

In addition to being capable of differentiating as neural cells (i.e., neurons, oligodendrocytes, astrocytes, and Schwann cells), the peripheral tissue-derived MSCs are capable of differentiating as non-neural cells that are normally not found in the tissue from which the cells were derived. For example, we have demonstrated that the skin-derived MSCs can differentiate as smooth muscle cells, cartilage, bone, muscle, and adipocytes. It is likely that the cells described herein have even greater potential. Conditions for the differentiation of the MSCs into smooth muscle cells, adipocytes, cartilage, bone, skeletal muscle, and cardiac muscle are described herein. Additionally, we show that the skin-derived MSCs can express RNA transcripts consistent with endodermal differentiation. These findings demonstrate that the skin-derived MSCs have potential to differentiate along all three germ layers.

Signals or conditions sufficient for inducing MSCs to differentiate as other cell types (e.g., lymphocytes, cardiac muscle cells, skeletal muscle cells, melanocytes, and pancreatic cells) are known in the art. For example, unique signals induce neural crest-derived stem cells to become melanocytes, cartilage, smooth muscle cells, or bone (for review, see LaBonne and Bronner-Fraser, J. Neurobiol., 36:175-189, 1998; Sieber-Blum, Intl. Rev. Cytol. 197:1-33, 2000). Conditions for inducing CNS-derived neural stem cells to differentiate as non-neural cells such as smooth muscle cells, skeletal muscle cells, hepatocytes, hematopoietic cells, osteocytes, and chondrocytes have similarly been elucidated (Bjornson et al., Science 283:534-537, 1999; Tsai and McKay, J. Neurosci. 20:3725-3735, 2000; Keirstead et al., J. Neurosci. 19:7529-7536, 1999; Mujtaba et al., Dev. Biol. 200:1-15, 1998; Clark et al., Science 288:1660-1663, 2000).

Our recent discovery that MSCs maintain the potential to produce both neural and non-neural cell types has been accompanied by the discovery that non-neural stem cells such as bone marrow-derived stem cells (i.e., stromal cells or mesenchymal stem cells) also have the potential to produce a wide variety of neural and non-neural stem cells (Ferrari et al., Science 279:1528-1530, 1998; Gussoni et al., Nature 401:390-394, 1999; Peterson et al., Science 284:1168-1170, 1999; Pereira et al., Proc. Natl. Acad. Sci. USA 92:4857-

Figure 13:
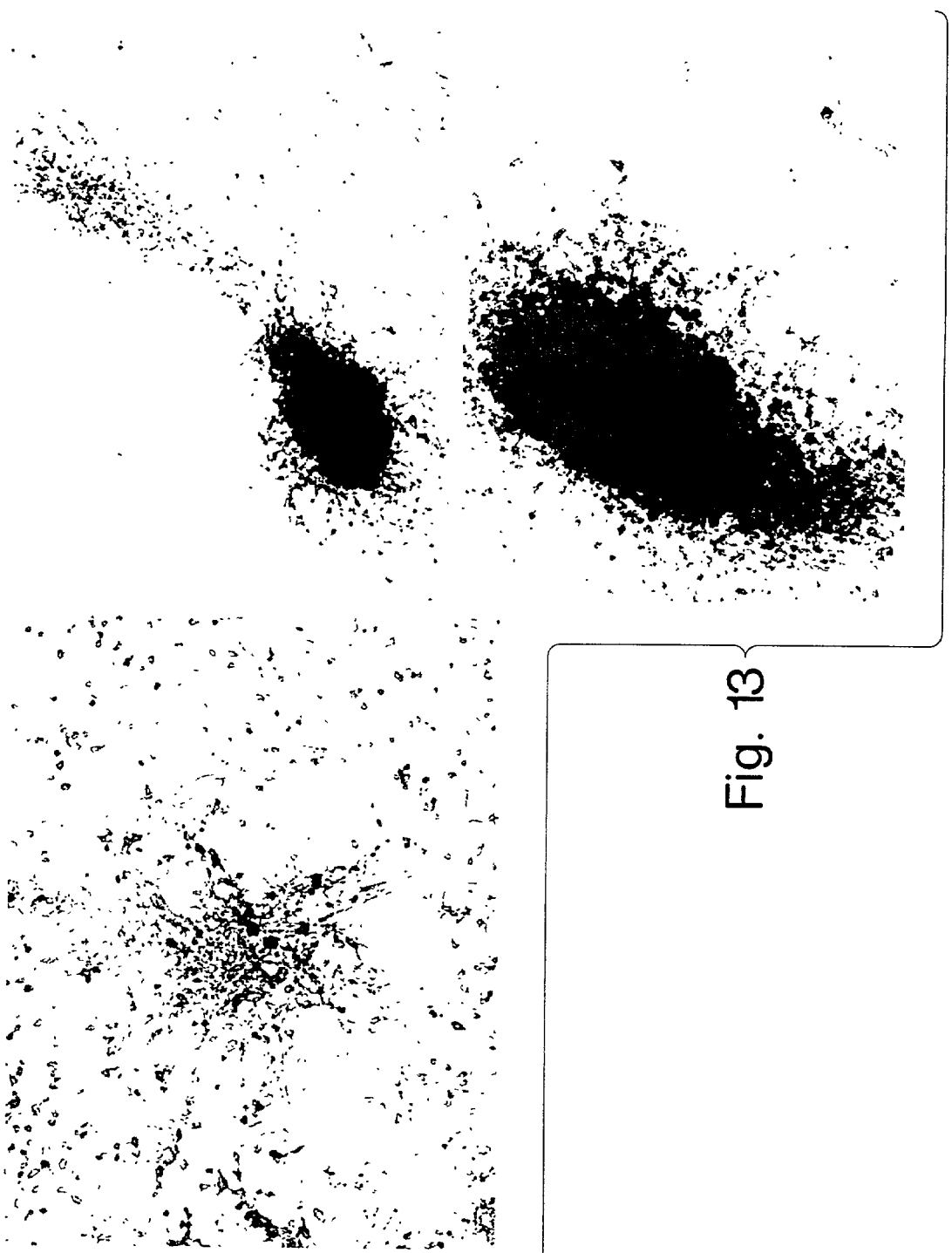
FIG. 13 are photographs of skin-derived stem cells plated in 15% FBS in the presence of skeletogenic supplements and cultured for two weeks. The cells are stained with Alcian Blue which reveals nodules of chondrocyte-associated acidic proteoglycans.
Figure 14:
FIG. 14 are photographs of skin-derived stem cells plated in 15% FBS in the presence of skeletogenic supplements and cultured for three weeks. The cells are stained with Alizarin Red which identified osteoblast-associated calcium accumulations.
Figure 14:
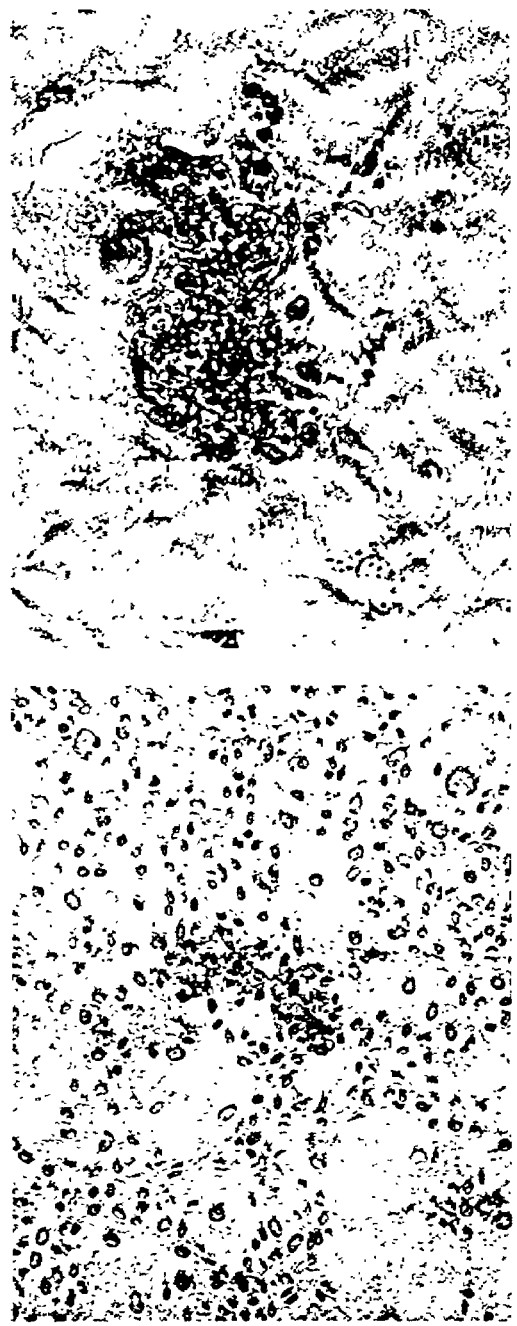
Figure 15:
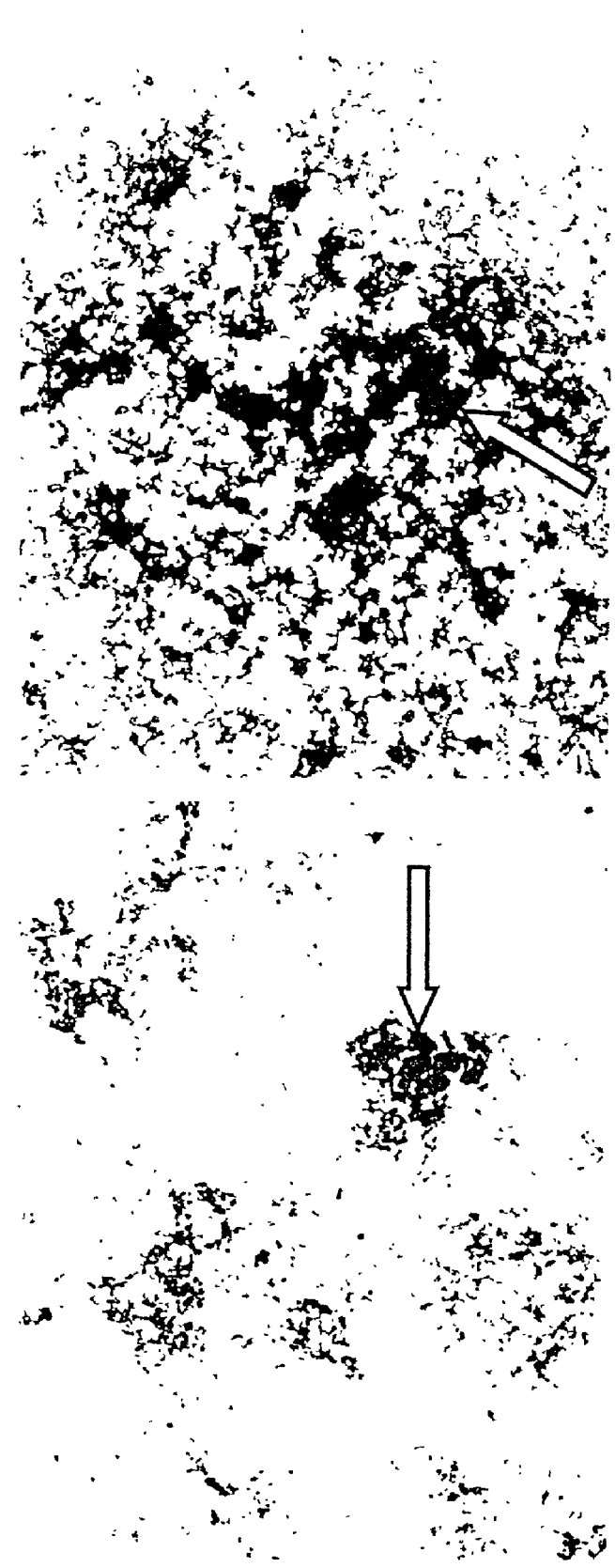
FIG. 15 are photographs of skin-derived stem cells plated in 15% FBS in the presence of skeletogenic supplements, cultured for three weeks, and co-stained with both Alcian Blue and Alizarin Red. Co-staining reveals that the calcium deposits occur within a layer of chondrocytic proteoglycan accumulation.
Figure 16:
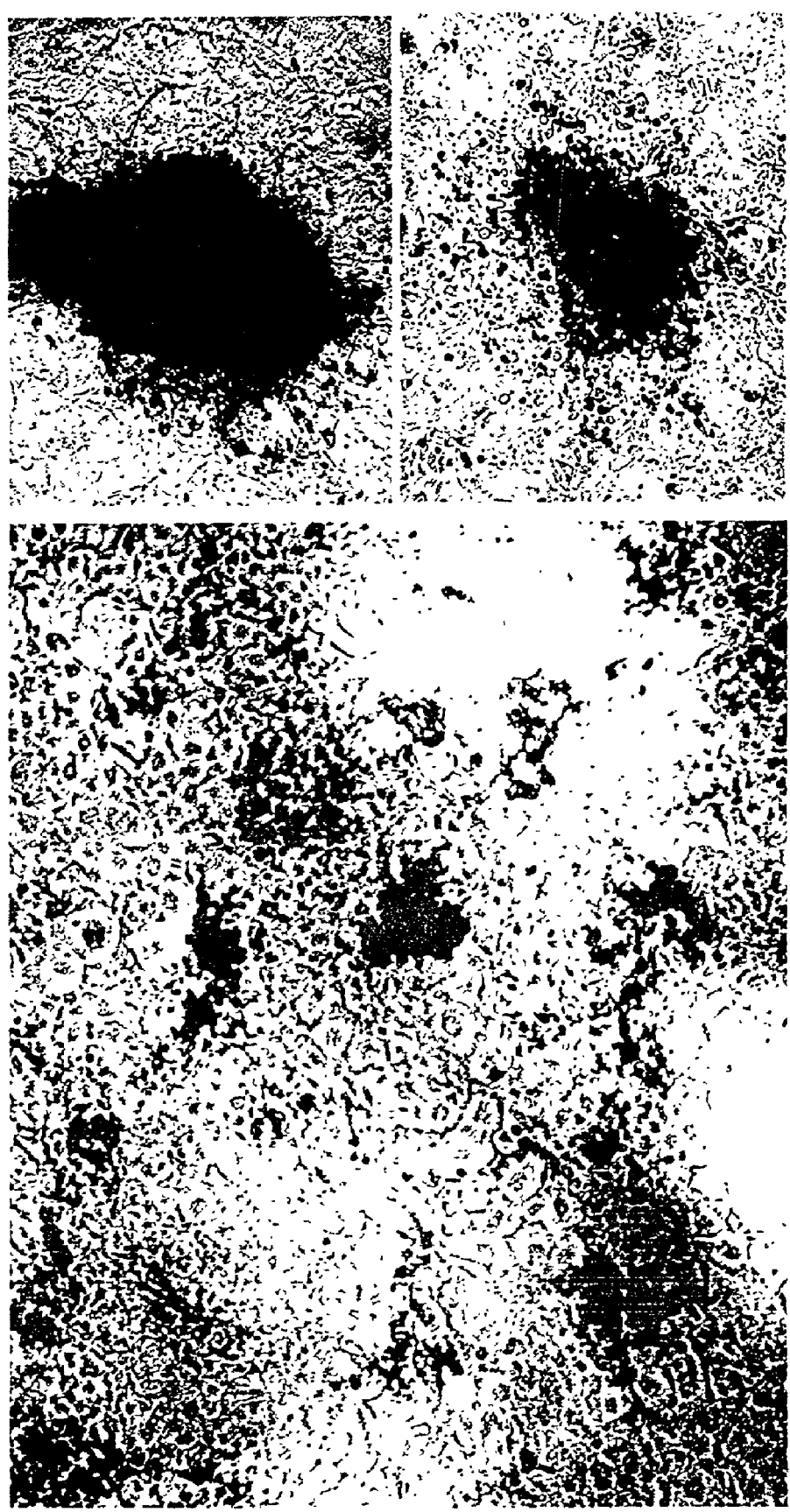
FIG. 16 are photographs of skin-derived stem cells plated in 15% FBS in the presence of skeletogenic supplements and cultured for 4-5 weeks, and demonstrate the formation of optically dense deposits indicative of bone formation.
Figure 17:
FIG. 17 shows that co-culture of GFP labeled skin-derived stem cells with cardiac myocytes induces expression of fetal cardiac actin. The expression of fetal cardiac actin co-localizes with GFP indicating that the differentiated cell is derived from the skin-derived stem cell.
Figure 17:
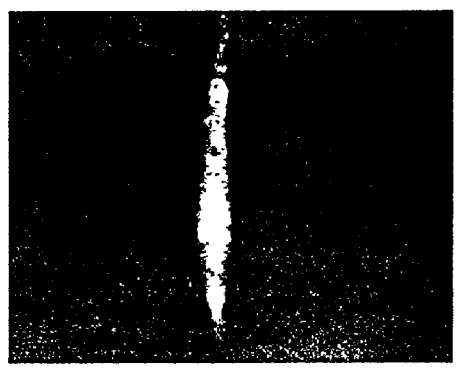
Figure 17:
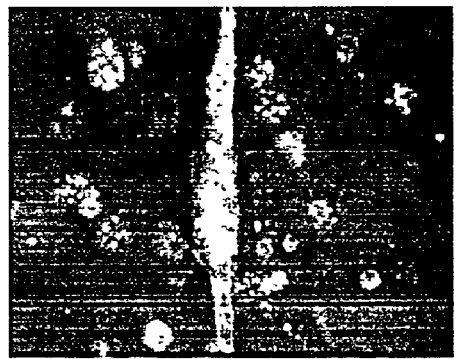
Figure 18:
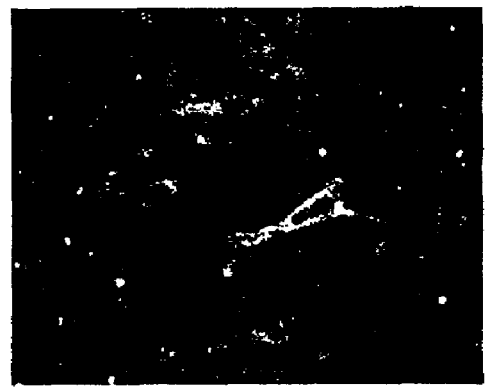
FIG. 18 shows that co-culture of GFP labeled skin-derived stem cells with C2C12 cells induces expression of desmin. The expression of desmin co-localizes with GFP, and the morphology of this desmin expressing cell is indicative of a skeletal muscle cell.
Figure 18:
Figure 18:
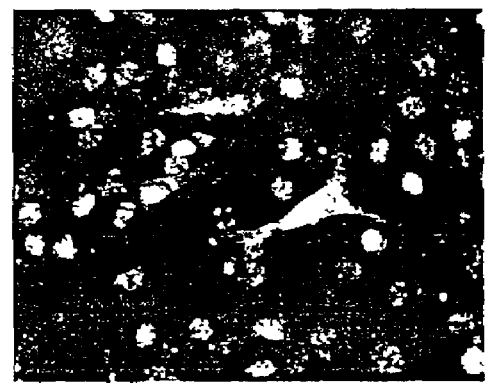
Figure 19:
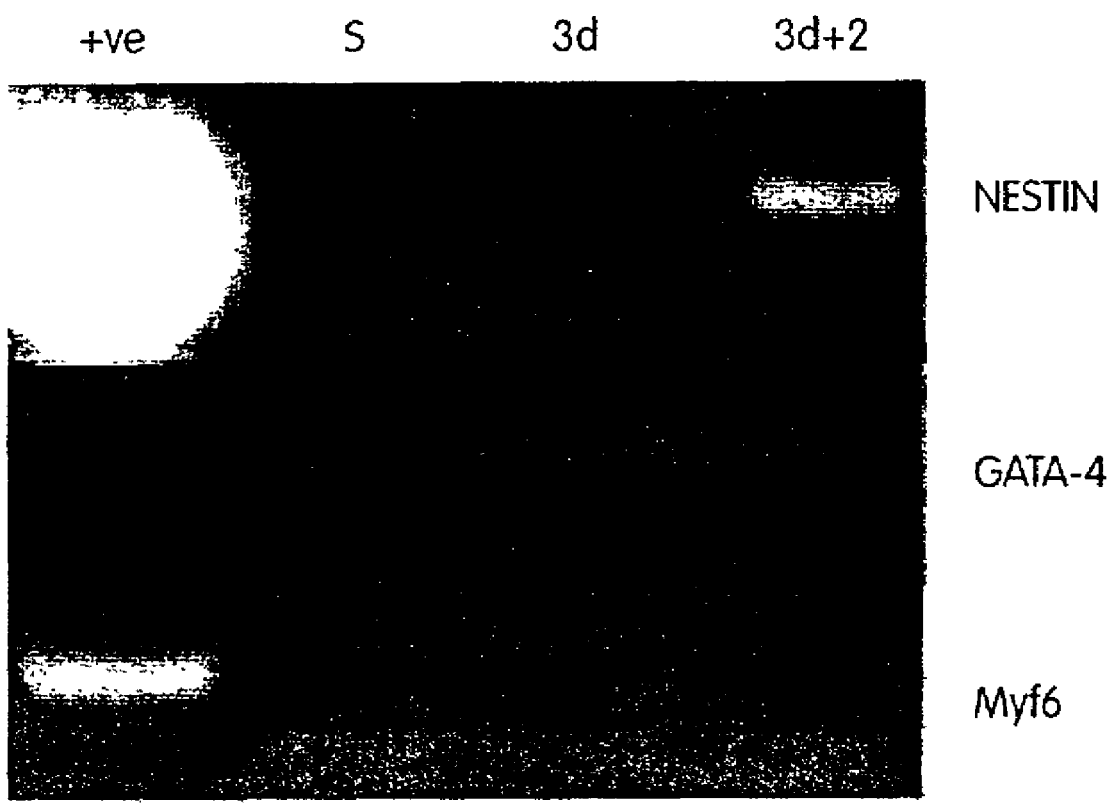
FIG. 19 shows RT-PCR analysis of skin-derived MSCs grown in spheres (S), plated in proliferation media for three days (3d), or plated in proliferation media for three days followed by two days in 5% serum (3d+2). The skin-derived MSCs express nestin, GATA-4, and Myf6. Positive controls (+ve) are: E10 brain (for nestin), embryoid bodies (for GATA-4), and muscle (for Myf6).
Figure 20:
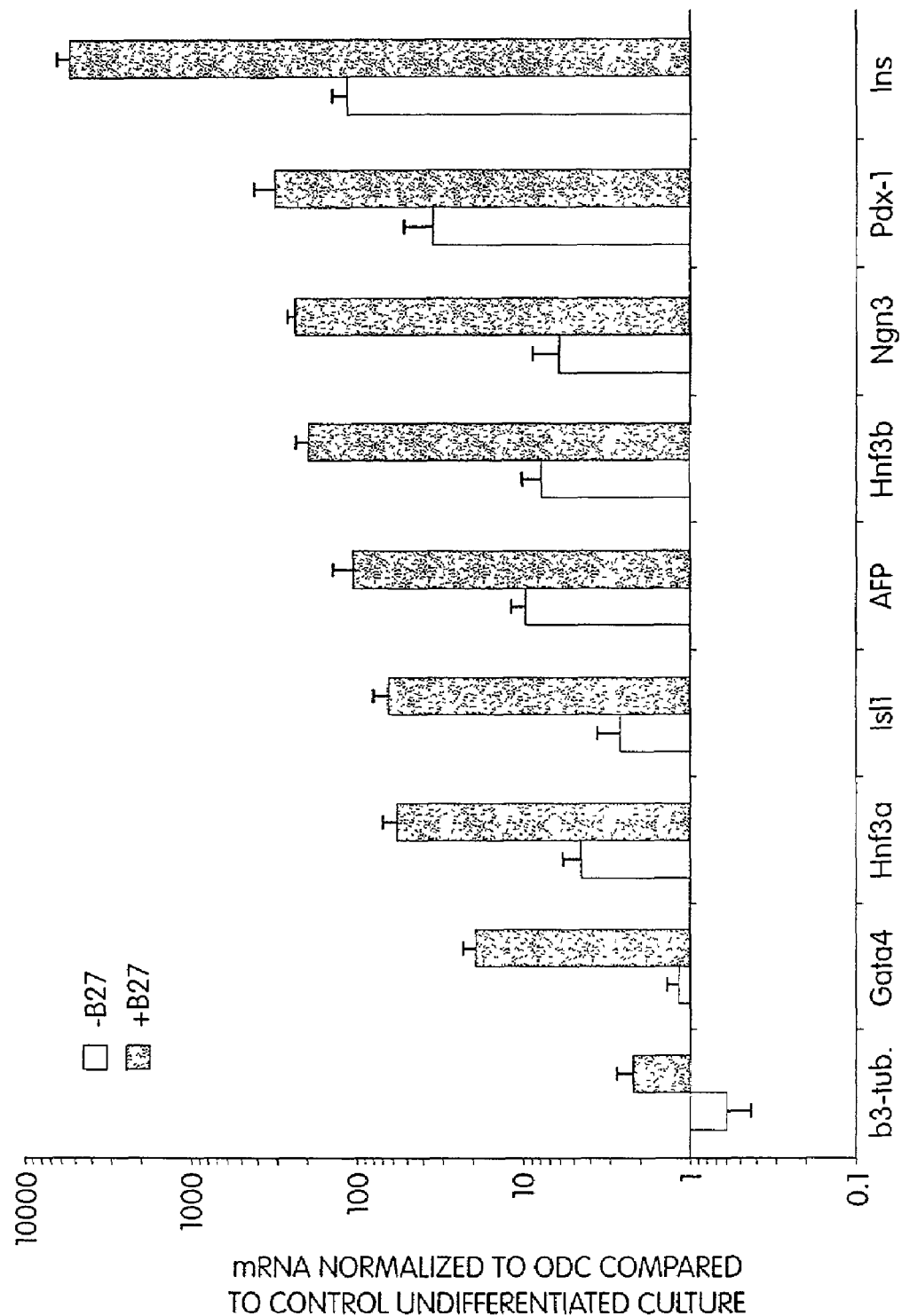
FIG. 20 shows that skin-derived MSCs express endodermal markers under certain differentiation conditions. Skin-derived MSCs were cultured under standard proliferation conditions in the presence or absence of B-27 supplement. Differentiation was induced by plating cells in the presence of nicotinamide, and the resulting differentiated cells were analyzed by quantitative RT-PCR. The graph demonstrates that skin-derived MSCs differentiated in the presence of nicotinamide express several markers of endodermal differentiation including GATA-4, HNF3α, Isl1, AFP, HNF3β, Ngn3, Pdx-1, and Insulin. Although cells proliferated in either the presence or the absence of B27 supplement can be induced to express endodermal markers, cells proliferated in B27 appear to express such markers to a higher degree.

4861, 1995; Prockop, Science 276:71-74, 1997; Kessler and Byme, Annu. Rev. Physiol. 61:219-242, 1999; Pittenger et al., Science 284:143-147). The peripheral tissue-derived MSCs described herein can be induced to differentiate into both neural and non-neural cells that are not normally found in the tissue from which the MSCs were derived.

a. MSCs can differentiate to smooth muscle: For induction of differentiation into smooth muscle cells, the cell clusters were centrifuged, the growth factor-containing supernatant removed, and the clusters resuspended in fresh media containing B-27 supplement and either 3% rat serum or 1-3% fetal bovine serum. The clusters were then plated onto dishes coated with poly-D-lysine/laminin, and the medium was changed every 3 to 7 days. Smooth muscle cells were identified by immunocytochemistry with an antibody to smooth muscle actin (SMA).

b. MSCs can differentiate to adipocytes: For induction of differentiation into adipocytes, the cell clusters were centrifuged, the growth factor-containing supernatant removed, and the clusters resuspended in fresh media containing B-27 supplement with 10% fetal bovine serum. The clusters were plated onto dishes coated with D-lysine/laminin. Differentiated adipocytes were identified by OilRed staining.

c. MSCs can differentiate to a skeletogenic fate:: For induction of differentiation along a skeletogenic lineage, the cell clusters were centrifuged, the growth factor containing supernatant removed, and the clusters resuspended in fresh media containing B-27 supplement with 15% fetal bovine serum including skeletogenic supplements. The skeletogenic supplement includes dexamethasone (100 nM), ascorbic acid (50 nM), and b-glycerophosphate (10 mM). After 2 weeks, Alcian Blue staining of the cultures reveals nodules of staining characteristic of chondrocytes. Alcian Blue staining indicates that the chondryocytes produce acidic proteoglycans (FIG. 13). After 3 weeks, calcium accumulation is observed in the cultures indicative of osteoblast activity. The calcium accumulation is assayed by Alizarin Red S staining (FIG. 14). Alcian Blue/Alizarin Red co-staining at 3 weeks demonstrates that the calcium accumulation occurs within a layer of chondrocytic proteoglycans (FIG. 15). Finally, by about 4-5 weeks, optically dense deposits, indicative of bone formation, are observed in the culture (FIG. 16).

d. MSCs can give rise to muscle: To assess the ability of the skin-derived stem cells of the invention to differentiate along a muscle lineage, we co-cultured GFP-labelled skin-derived stem cells with either cardiac myocytes or with C2C12 skeletal myoblasts. After several days of co-culture the skin-derived stem cells were analyzed based on both morphology and on protein expression. Cells co-cultured with cardiac myocytes express fetal cardiac actin, and the fetal cardiac actin expression co-localizes with GFP (indicating that the expressing cells are derived from the skin-derived precursors) (FIG. 17). Fetal cardiac actin is expressed in both cardiac and skeletal muscle, and the morphology of these cells is consistent with either two cardiac muscle cells or with a single multinucleated skeletal myotube. However these results indicate that skin-derived stem cells can differentiate to a muscle cell type. Cells co-cultured with C2C12 cells give rise to desmin positive cells, and desmin expression co-localizes with GFP (FIG. 18). The morphology and protein expression of the skin-derived stem cells cultured in this manner is consistent with their differentiation to skeletal muscle. These experiments indicate that skin-derived stem cells can differentiate to produce skeletal muscle, and likely can also differentiate to produce cardiac muscle.

e. MSCs can express endodermal markers: We have shown that the skin-derived MSCs of the invention can differentiate to give rise to both neural and non-neural cells. We have presented six examples of mesodermal cell types that arise from differentiation of the MSCs. We now present evidence that the MSCs can also express transcripts consistent with endoderm differentiation. FIG. 19 shows RT-PCR analysis demonstrating that MSCs express the endodermal marker GATA-4. In a second experiment, skin-derived MSCs were cultured under standard proliferation conditions in the presence or the absence of B-27 supplement. Cells were dissociated and plated in media supplemented with nicotinamide. Differentiated cells were analyzed by RT-PCR for the expression of several endodermal markers including GATA-4, HNF3α, Isl1, AFP, HNF3β, Ngn3, Pdx-1, and Insulin. FIG. 20 summarizes the results of this experiment which demonstrates that cells differentiated in the presence of nicotinamide express markers of endodennal differentiation. Additionally although endodermal differentiation is observed in cells that were proliferated in either the presence or the absence of B27 supplement, the cells proliferated in the presence of B27 expressed higher levels of endodermal markers than cells proliferated in the absence of B27. This data demonstrates that the skin-derived MSCs of the invention can differentiate to cell types derived from all three germ layers. Additionally, these experiments demonstrate that the modulating of multiple plating conditions (in this case the addition of both B27 supplement and nicotinamide), at different times, can effect the differentiation of the skin-derived MSCs.

Skin-derived MSCs can differentiate to cell types of both neural and non-neural lineages. We demonstrate that the MSCs can give rise to several different non-neuronal cell types including smooth muscle cells, adipocytes, cartilage, bone, skeletal muscle, and cardiac muscle. Additionally, we show that the skin-derived MSCs can express transcripts consistent with endoderm differentiation. The tremendous differentiative potential of skin-derived MSCs suggests that in addition to the many cell types shown here, MSCs can also give rise to other mesodermal and endodermal cell types. Furthermore, these results demonstrate that changes in plating conditions (i.e., alterations in serum concentrations, the addition of pharmacological agents and small molecules, and/or co-culturing cells with other cell types) can have dramatic effects on cell proliferation, differentiation and/or survival.

EXAMPLE 16

Contacting MSCs with Agents to Influence Differentiation

As described in detail above, the proliferation, differentiation, or survival of the cells of the invention can be influenced by modulating the culture conditions. For example, we have shown that changes in the plating conditions, or the addition of pharmacological agents to the culture medium influences the proliferation, differentiation and/or survival of MSCs.

We show that the proliferation, differentiation or survival of MSCs can also be influenced by contacting the cells with a therapeutic protein including one or more cytokine, growth factor, extracellular protein, etc. One of skill will recognize that the concentration of these agents can be altered to determine the optimal dose. Additionally, the therapeutic proteins may be added alone, or in combination, and combinations of proteins may be administered simultaneously or at varying timepoints.

Figure 21:
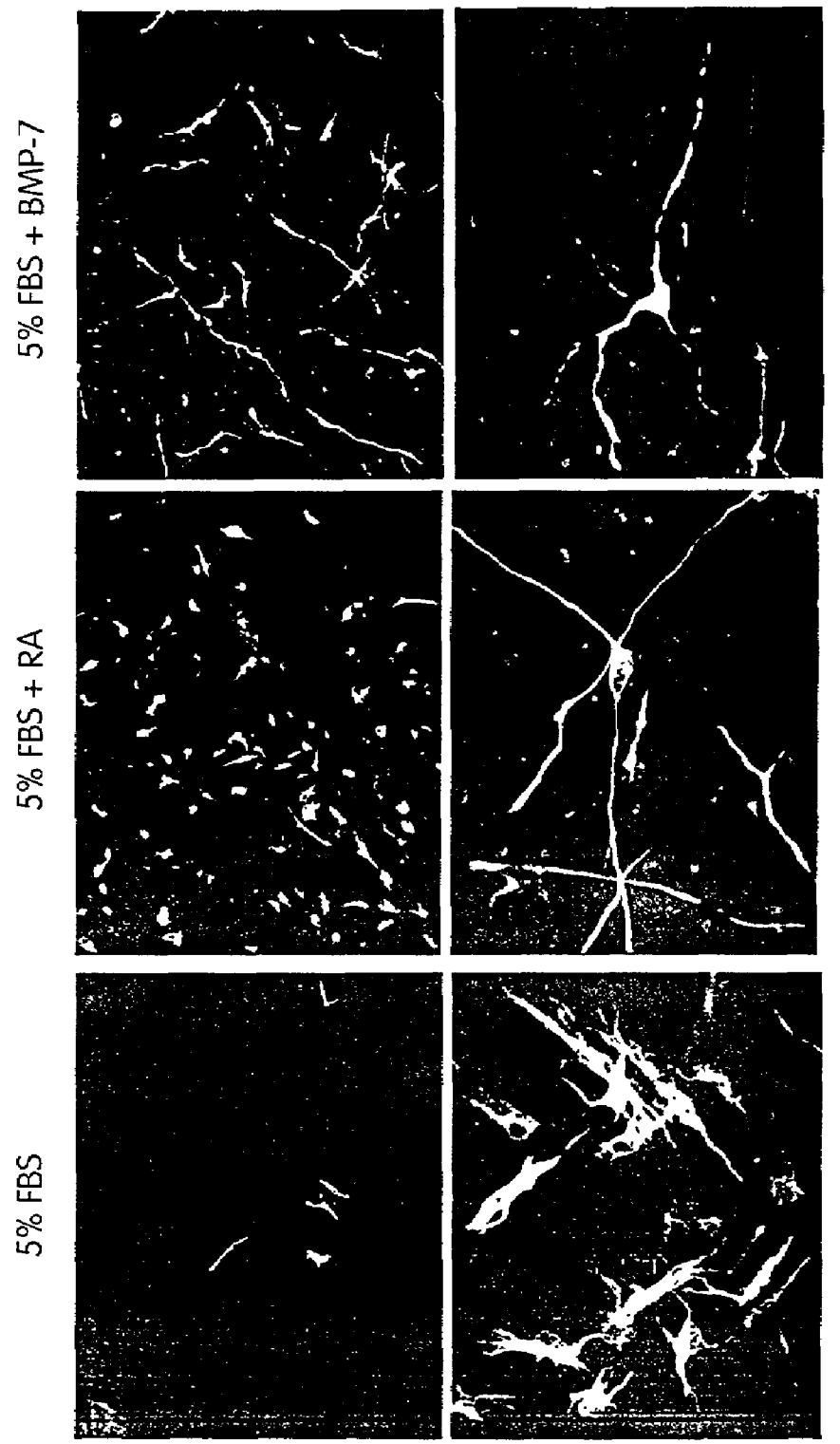
FIG. 21 shows that agents, including therapeutic proteins and small molecules, influence the proliferation, differentiation, and/or survival of skin-derived stem cells. Cells were dissociated and plated in the presence of either 5% FBS, 5% FBS+ retinoic acid (RA), or 5% FBS+BMP7. Cells were analyzed immunocytochemically for expression of neurofilament M (NFM). Note the bottom panels shows a 40× magnification of the cells.

Skin derived MSCs were obtained and cultured as described in detail above. To induce differentiation, cells were plated in the presence of 5% serum supplemented with either retinoic acid or BMP-7. Neuronal differentiation was analyzed using a polyclonal anti-neurofilament antibody. Addition of either retinoic acid or BMP-7 enhances the number and complexity of neurofilament positive cells, in comparison to cells differentiated in the presence of serum alone (FIG. 21).

EXAMPLE 17

Skin-Derived MSCs are a Distinct Population of Stem Cells

We have demonstrated that the skin-derived multipotent stem cells of the invention can differentiate to produce both neural and non-neural cell types. Furthermore, we have demonstrated that these skin-derived stem cells can produce at least six mesodermal cell types (smooth muscle, adipocyte, cartilage, bone, skeletal muscle, and cardiac muscle). The ability of the stem cells of the invention to differentiate along mesodermal lineages is a characteristic of mesenchymal stem cells previously isolated from sources including bone marrow.

Although previous experiments using mesenchymal stem cells indicate that such cells are selectively adherent (in contrast to the skin-derived cells of the invention), we performed morphological and immunocytochemical analysis to demonstrate that the skin-derived cells of the invention are distinct from the mesenchymal stem cells previously identified. Bone marrow derived mesenchymal stem cells were obtained from BioWhittaker, and were cultured under the conditions described herein for skin-dervied stem cells.

When grown under identical conditions, the two cell populations have significantly different morphology and growth characteristics. The mesenchymal stem cells do not proliferate in suspension when cultured under conditions which allow the skin-derived stem cells to grow as non-adherent clusters as described in detail herein. The cells were dissociated and plated overnight under the conditions described for the skin-derived cells. The two cell types are morphologically distinct: the skin-derived cells are considerably smaller while the mesenchymal stem cells have a more flattened appearance. Additionally although mesenchymal stem cells rapidly proliferate in standard mesenchymal cell medium, they survive but do not readily proliferate under the conditions used here.

Figure 22:
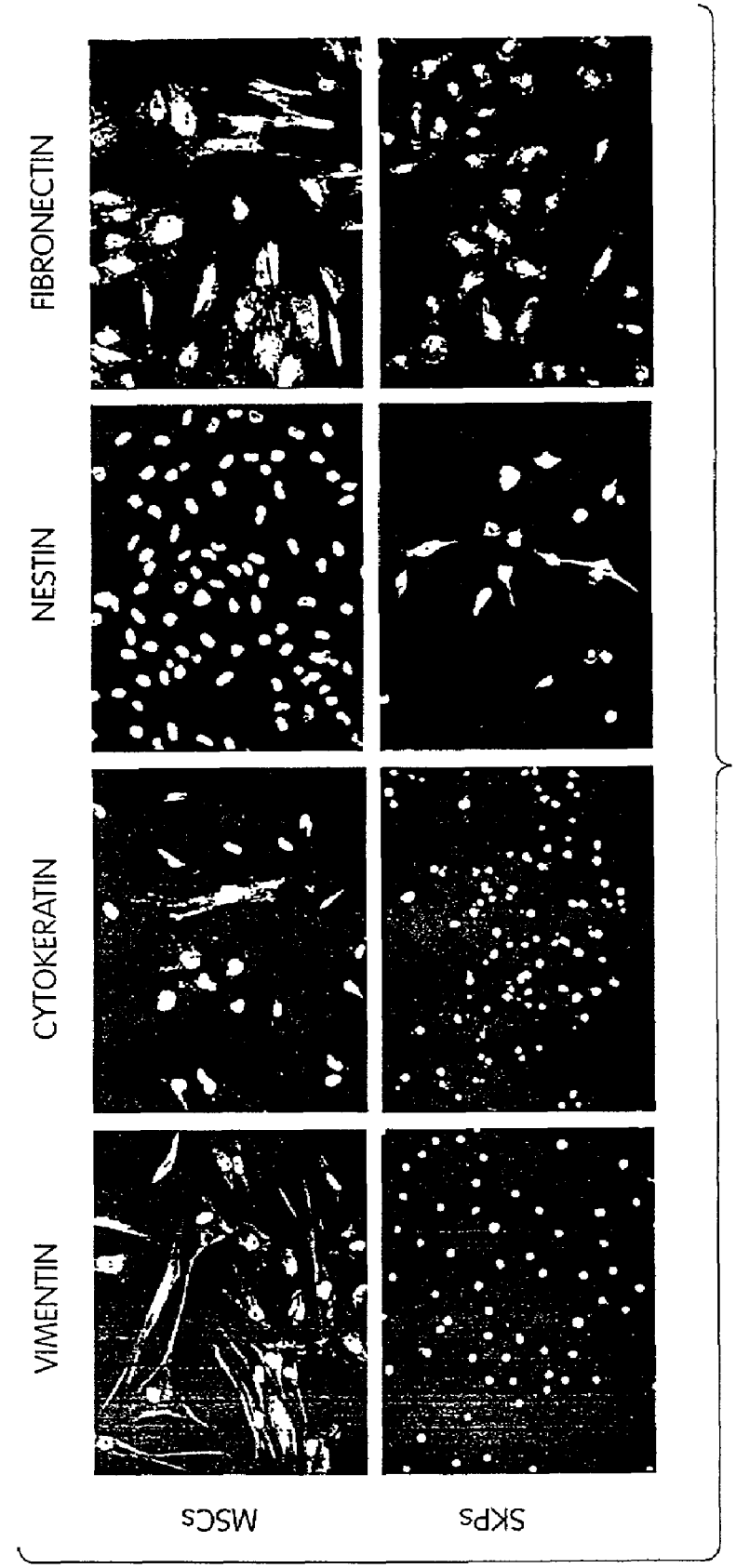
FIG. 22 shows that the skin-derived stem cells of the invention are a cell population distinct from mesenchymal stem cells. Mesenchymal stem cells and skin-derived stem cells were cultured under identical conditions, and immunocytochemical analysis was performed using antibodies to nestin, fibronectin, vimentin, and cytokeratin. The top panels are photographs of mesenchymal stem cells, and the bottom panels are photographs of the skinderived stem cells. Note not only the differences in protein expression, but also the differences in morphology between the two cell types.

Immunocytochemical analysis further illustrates the differences between these two cell types. Cells were dissociated, plated overnight, and analyzed immunocytochemically for the expression of vimentin, cytokeratin, nestin, and fibronectin. Both mesenchymal stem cells and the skin-derived multipotent stem cells of the invention express fibronectin. However, the two cell types differed in the expression of the other three markers analyzed. Skin-derived stem cells express nestin (mesenchymal stem cells do not). Mesenchymal stem cells express vimentin, and a sub-set of the mesenchymal stem cells in culture express cytokeratin (skinderived stem cells express neither vimentin nor cytokeratin) (FIG. 22).

Despite the ability of skin-derived stem cells to differentiate along several mesodermal lineages, the stem cells of the invention are distinct from previously identified mesenchymal stem cells. These differences are demonstrated by the differential morphology and protein expression observed when mesenchymal stem cells are cultured under the conditions described herein for the proliferation and differentiation of skin-derived stem cells.

EXAMPLE 18

Isolation of Skin-Derived Multipotent Stem Cells from Human Foreskin

We have previously demonstrated that the multipotent stem cells of the invention can be isolated from both rodent and human skin. Exemplary samples have been obtained from the scalp, back, and abdomen of donors. One of the unique advantages of the present invention is that skin represents a plentiful and easily accessible source of autologous or heterologous stem cells for transplantation.

However, in addition to autologous or heterologous skin samples taken specifically to generate stem cells for transplantation, skin samples are routinely harvested from healthy donors in the course of many medical procedures. Such samples represent a plentiful source of tissue for the generation of skin-derived stem cells. Such stem cells, or the differentiated progeny thereof, could be used for research purposes, as well as for autologous or heterologous transplantation. Exemplary procedures which generate excess skin include circumcision and cosmetic surgery (e.g., face lifts, liposuction, and "tummy tucks"). Typically, the excess tissue generated following these procedures is removed and discarded from otherwise healthy patients.

In one embodiment, stem cells can be isolated and cultured from said excess tissue. Such stem cells, or the differentiated progeny thereof, can be used immediately for transplantation or research purposes. Alternatively, the stem cells, or the differentiated progeny thereof, can be banked for later use by the donor (autologous transplantation), or for the treatment of a related or unrelated recipient.

In another embodiment of the present invention, stem cells are harvested from the foreskin of a male patient. The stem cells, or the differentiated progeny thereof, can be stored for later use by either the same male patient or his blood relatives. Alternatively, the stem cells, or the differentiated progeny thereof, can be used for the treatment of an unrelated recipient.

Foreskin samples from human patients were obtained from surgeons performing circumcisions. The samples were taken from males ranging in age from newborns to adolescents. We note that we have generated proliferating cultures of non-adherent skin-derived stem cells from 21 samples, and have not observed any significant differences in the survival, proliferation, or differentiation characteristics among the cultures based on the age of the donor.

The quantity of tissue obtained following circumcision is relatively small. Accordingly, we reasoned that the number of stem cells in said tissue may be relatively low, and that the survival of cultures derived from these samples may improve if the stem cells could be enriched in relation to non-stem cells in the sample. Previous studies demonstrated that skin-derived stem cells reside in the dermal layer of the skin. Thus, we employed a novel method for isolating and culturing stem cells from limiting quantities of tissue. Briefly, foreskin samples were first cut into pieces and then enzymatically digested to separate the dermal and epidermal layers. Specifically, we digested the tissue for 24-48 hours at 4° C. in an enzyme blend containing collagenase and either Dispase or thermolysin. However, one of skill in the art can readily select from among commercially available proteases to choose one or more enzymes which would achieve a similar effect. Following separation of the dermal and epidermal layer, the dermal layer was dissociated by further digestion in the enzyme blend for 30 minutes at 37° C. followed by trituration to release single cells.

Figure 23:
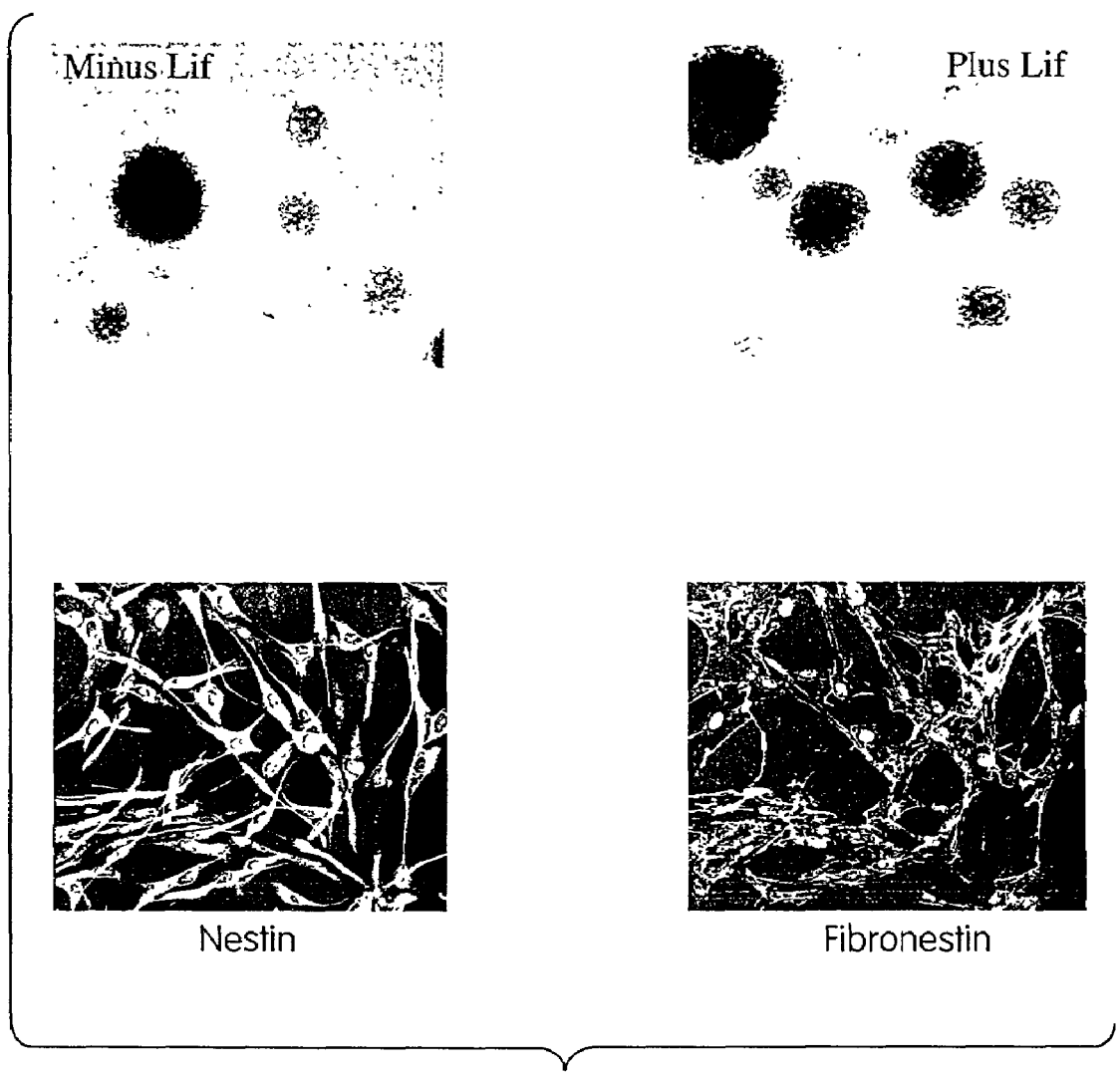
FIG. 23 shows that skin-derived stem cells isolated from human foreskin proliferate as non-adherent clusters in culture. The top panels show that skin-derived stem cells specifically isolated from the dermal layer of human foreskin proliferate as non-adherent clusters. In contrast to human central nervous system derived stem cells, the survival and proliferation of human skin-derived stem cells is not dependent on LIF. The bottom panels show that skin-derived stem cells isolated from foreskin express nestin and fibronectin.

We cultured the cell suspension, as previously described, in non-adherent vessels in the presence of EGF and FGF2. FIG. 23 demonstrates that skin-derived stem cells harvested from human foreskin proliferate as non-adherent clusters. The clusters are morphologically indistinguishable from skin-derived stem cells derived from rodent tissue. Skin-derived clusters are loosely compacted, and the cells can be readily dissociated manually without the use of proteases. Such characteristics appear to distinguish skin-derived clusters from CNS-derived neurospheres. Note that we have cultured these proliferating skin-derived stem cells in the presence and absence of LIF, and have observed no significant differences in their proliferation, differentiation or survival characteristics. Furthermore, we have currently passaged and maintained foreskin derived stem cells as proliferating cultures for greater than three months.

One of the characteristics of skin-derived stem cells isolated from rodents or other human tissue is the differentiation capacity of these cells. We have previously demonstrated that skin-derived stem cells can differentiate along a range of neuronal and non-neuronal fates. Similarly, foreskin-derived stem cells can differentiate along a wide range of neuronal and non-neuronal fates.

Figure 24:
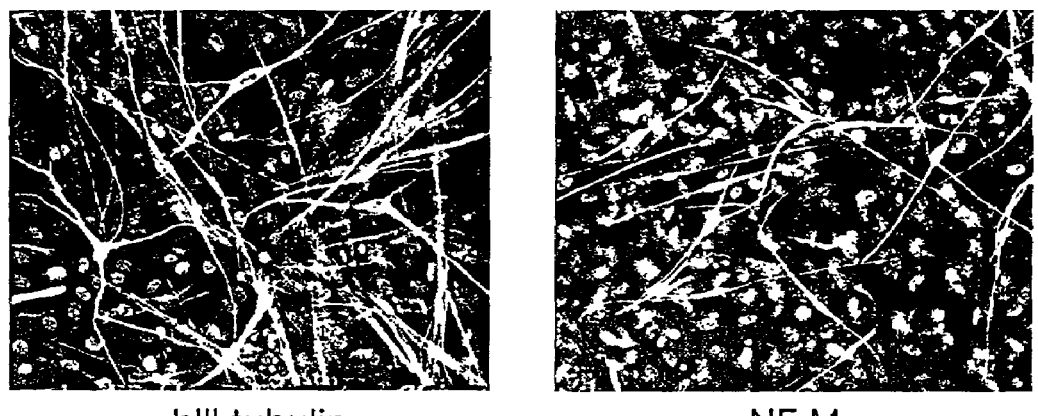
FIG. 24 shows that skin-derived stem cells isolated from human foreskin differentiate to form highly morphologically complex neurons as assayed by expression of bIII-tubulin and neurofilament-M (NF-M).
Figure 25:
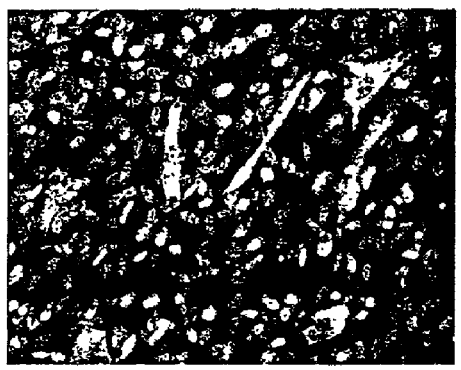
FIG. 25 shows that skin-derived stem cells isolated from human foreskin differentiate to form glial cells as assayed by expression of GFAP and CNP.
Figure 25:
Figure 26:
FIG. 26 shows that skin-derived stem cells isolated from human foreskin differentiate to form additional neuronal cells types as assayed by expression of S100 and peripherin. S100 is a marker of bipolar cells and peripherin is a marker of peripheral neurons.
Figure 26:
Figure 27:
FIG. 27 shows that skin-derived stem cells isolated from human foreskin differentiate to form non-neural cell types as assayed by expression of smooth muscle actin.

The expression of various neural and non-neural markers was assayed following differentiation of foreskin-derived stem cells. Briefly, proliferating, non-adherent clusters were dissociated and plated on an adherent substratum in the presence of proliferation medium. After several days, the medium was changed to differentiation medium (5% fetal bovine serum/no mitogens), and marker expression was analyzed during this differentiation phase. Our results indicate that foreskin derived stem cells can differentiate along a wide range of neuronal and non-neuronal cell types. These results are consistent with our finding for the differentiation potential of skin-derived stem cells obtained from rodents and other human tissue samples. For example, under differentiation conditions, foreskin derived stem cells can express nestin, fibronectin, bIII-tubulin, neurofilament-M, GFAP, CNP, S100, peripherin, and smooth muscle actin (FIGS. 23-27). The expression of bill-tubulin and neurofilament-M, in combination with the morphology of these cells, is indicative of the formation of highly complex neurons (FIG. 24). The expression of GFAP and CNP demonstrate the ability to give rise to glial cell types (FIG. 25). The expression of S100 and peripherin indicates that foreskin-derived stem cells can generate additional neuronal cell types including bipolar cells (S100) and peripheral neurons (peripherin) (FIG. 26). Finally, the expression of the normeural marker smooth muscle actin (FIG. 27) indicates that, as has been observed for other skin-derived stem cells, foreskin-derived stem cells have extensive differentiation capacity and can give rise to both neural and non-neural cell types.

The foregoing experiments were performed using the following methods, except where otherwise noted.

Skin-Derived MSC Culture

For neonatal (three to 14 days) and adult (two months to one year) mice, skin from abdomen and back was carefully dissected free of other tissue, cut into 2-3 mm$^3$ pieces, washed three times in HBSS, and then digested with 0.1% trypsin for 40 minutes at 37 C, followed by 0.1% DNAase for one minute at room temperature. Tissue pieces were then washed twice with HBSS, once with media (DMEM-F12, 3:1, 1 g/ml fungizone, 1% penicillin/streptomycin) containing 10% rat serum (Harlan Bioproducts), and twice with serum-free media. Skin pieces were then mechanically dissociated in media, and the suspension poured through a 40 M cell strainer (Falcon). Dissociated cells were centrifuged, and resuspended in 10 ml media containing B-27 supplement, 20 ng/ml EGF and 40 ng/ml bFGF (both Collaborative Research). Cells were cultured in 25 cm$^2$ tissue culture flasks (Coming) in a 37 C, 5% $CO_2$ tissue culture incubator.

To culture human skin-derived MSCs, two to three pieces of scalp tissue ranging between 4-9 mm$^2$ (generated by placement of the stereotaxic apparatus for neurosurgery) were washed with HBSS, any subcutaneous tissue was removed, and the skin was cut into small pieces 1-2 mm$^3$ in size. Tissue pieces were transferred to 15 mL Falcon tubes, washed three times with HBSS, and enzymatically digested in 0.1% trypsin for 40 minutes at 37 C, and then washed as for mouse tissue. Dissociated cells were suspended in 5 mL of the same media used for mouse cultures, with the addition of 20 ng/ml LIF (R&D Systems Inc.). The cell suspension was placed in Falcon 6-well tissue culture plates and maintained in a 37 C, 5% $CO_2$ tissue culture incubator. Cells were subcultured by partial dissociation of the clusters that formed every 7 to 10 days.

To passage floating clusters of cells, the medium containing the cell clusters was centrifuged, the cell pellet mechanically dissociated with a fire-polished Pasteur pipette, and the cells reseeded in fresh media containing B-27 supplement and growth factors as above. Cells were passaged every 6 to 7 days. For induction of differentiation into smooth muscle cells, the cell clusters were centrifuged, the growth factor-containing supernatant removed, and the clusters resuspended in fresh media containing B-27 supplement and either 3% rat serum or 1-3% fetal bovine serum. The clusters were then plated onto 4-well Nunclon culture dishes coated with poly-D-lysine/laminin, and the medium was changed every 3 to 7 days.

Transplantation of Olfactory Epithelium-Derived MSCs

Olfactory epithelium-derived MSCs were purified and cultured as described herein. Female Sprague-Dawley rats or CD1 albino mice (Charles River, Montreal, Quebec, Canada) weighing 180-200 g or 25-30 g, respectively, were anaesthetized with a mixture of ketamine (90 mg/kg) and xylazine (10 mg/kg) (intraperitoneal) prior to stereotactic injections of 24 µg of 6-hydroxydopamine hydrobromide (dissolved in 5 µL of 0.9% saline containing 0.2 mg/ml ascorbate) into the right medial forebrain bundle (Tooth bar:-2.4 mm; A:-4.4 mm; L: 1.0 mm; V:7.5 mm). Two weeks after the lesion, animals were tested for rotational behavior. Animals were immunosuppressed with cyclosporine (40 mg/kg, intraperitoneal) once a day until the day of sacrifice. For MSC transplantation, anaesthetized animals were mounted in a Kopf stereotactic apparatus, and 2×2.5 µL aliquots of MSCs were injected unilaterally into the lesioned caudate putamen or bilaterally in some animals. The injections were made using a 5 µL Hamilton syringe at the following coordinates: Tooth bar, −2.4 mm; A: 0.2; L: 3.0; V: 5.5-6.0. Injections were performed over a period of three minutes, a further five minutes was allowed for diffusion, and the needle was then retracted. These 5 µL injections contained MSCs derived from one neonatal pup cultured for 7 to 14 days. For the BrdU experiments, BrdU (10 µM) was added to culture media for 18 hours, after which the MSCs were washed three times with fresh media to remove the BrdU, and then transplanted one day later.

Transplantation of Skin-Derived MSCs

Labeling of skin-derived MSCs was performed as follows. Three days prior to transplantation, free-floating cell clusters were partially dissociated by gentle trituration, and then exposed to 50 MOI of a recombinant adenovirus expressing GFP, using standard techniques. Twenty-four hours later, the MSCs were centrifuged, washed, and resuspended in fresh medium containing 2 µM BrdU for an additional two days. Prior to transplantation, MSCs were rinsed five times with fresh medium and resuspended to a concentration of 50,000 cells/µl. At the time of transplantation, approximately 75% of the MSCs expressed GFP, while 95% were BrdU positive.

MSCs labeled with BrdU and GFP were stereotaxically injected into the right lateral ventricle of cryoanaesthetized two day old rat pups (co-ordinates from Bregma: lateral 1.5 mm, ventral 3.3 mm). Approximately 50,000 cells were injected over a three minute period in a volume of 1 µL. Fourteen days following transplantation, mice were perfused with 50 mL 4% formaldehyde buffered with PBS. Fifty micron coronal sections through the forebrain were cut using a freezing microtome and analyzed immunocytochemically. All eight animals receiving cell transplants showed extensive labeling for tagged cells. No evidence of tumor formation was observed.

Immunostaining

Immunostaining of olfactory epithelium-derived MSCs was performed as follows. With the exception of GC immunocytochemistry, culture dishes were washed twice with Tris-buffered saline (TBS; 10 mM Tris, 150 mM NaCl, pH 8), then fixed with 4% formaldehyde, washed three times with TBS, blocked with TBS plus 2% goat serum (Jackson ImmunoResearch, Mississuagua, Ontario, Canada), and 0.1% Triton-X (Sigma Chemicals, St. Louis Mo.) for 30 minutes, then incubated with primary antibody in TBS plus 2% goat serum. Following primary antibody incubation, the dishes were washed three times with TBS, incubated in secondary antibody in TBS plus 2% goat serum, washed three times, and then viewed with a fluorescence inverted microscope. The antibodies to GFAP (Boehringer Mannheim,Laval, Quebec, Canada), βIII tubulin (Sigma), NeuN (Dr. R. Mullen), MAP-2 (clone AP-20; Sigma), and NF-160 (American Tissue Culture Collection, Manassas Va.) were monoclonal antibodies used at concentrations of 1:200; 1:25; 1:10, and 1:1 respectively. Antibodies to nestin (a gift from Dr. Ron MacKay (National Institutes of Health), TH (Eugenetech Eugene, Oreg.), and DBH (Eugenetech) were rabbit polyclonal antibodies used at concentrations of 1:1000, 1:200, and 1:200 respectively. Secondary antibodies Cy3 conjugated goat anti-mouse (Jackson ImmunoResearch) and Cy3 conjugated goat anti-rabbit (Jackson ImmunoResearch), and were used at 1:1500. For double-labelling experiments, we used FITC goat anti-mouse (Jackson ImmunoResearch).

For GC immunocytochemistry, living cultures were incubated in DMEM containing HEPES, 5% heat inactivated horse serum (HS), and 1:10 GC antibody for 30 min at 37 C, washed three times with the medium/HEPES/HS, fixed with 4% formaldehyde for 15 minutes, rinsed three times in TBS, incubated in Cy3 conjugated goat anti-mouse antibody (1:1500) for two hours, and finally washed three times in TBS. Cultures processed for immunocytochemistry without primary antibodies revealed no staining.

Immunocytochemical analysis of cultured skin-derived MSCs was performed as follows. The primary antibodies that were used were: anti-nestin polyclonal (1:250, Dr. Ron McKay, NINDS), anti-nestin monoclonal (1:400, PharMingen Inc.), anti-βIII-tubulin monoclonal (1:500, Tuj1 clone, BabCo), anti-neurofilament-M polyclonal (1:200, Chemicon Intl.), anti-GAD polyclonal (1:800, Chemicon Intl.), anti-NSE polyclonal (1:2000, Polysciences Inc.), anti-GFAP polyclonal (1:200, DAKO), anti-CNPase monoclonal (1:400, Promega), anti-p75NTR polyclonal (1:500, Promega), anti-SMA monoclonal (1:400, Sigma-Aldrich), and anti-A2B5 monoclonal (Dr. Jack Snipes, M.N.I.). The secondary antibodies were Cy3-conjugated goat anti-mouse (1:200), Cy3-conjugated goat anti-rabbit (1:400), FITC-conjugated goat anti-mouse (1:50-1:100), and FITC-conjugated goat anti-rabbit (1:200) (all from Jackson Immunoresearch Laboratories).

Immunocytochemical analysis of free-floating brain sections was performed by DAB immunohistochemistry. For GFP, sections were incubated in 0.3% $H_2O_2$ for one hour to inhibit endogenous tissue peroxidase activity prior to blocking. For BrdU immunohistochemistry, sections were pre-incubated in 0.5% sodium borohydride for 20 minutes prior to blocking of endogenous peroxidase activity in 0.03% $H_2O_2$ for 30 minutes. To permeabilize the nuclei for BrdU immunohistochemistry, sections were incubated in 1% DMSO for 10 minutes, the DNA denatured with 2N HCl for 60 minutes, and the HCl neutralized with 0.1M borate buffer for 5 minutes. All sections were blocked for one hour in 10% BSA, and then incubated for 48 hours at 4° C. with either anti-GFP (1:1000, Clontech) or anti-BrdU (1:100, Becton-Dickinson). Primary antibodies were detected using a biotinylated horse anti-mouse secondary antibody (1:200, Vector Laboratories) for one hour at room temperature, and visualized using the Vectastain kit (Vector Laboratories) and a nickel-enhanced DAB reaction containing 0.05% DAB, 0.04% nickel chloride, and 0.015% $H_2O_2$. Sections were mounted onto slides, dehydrated through a series of ethanols and Histoclear (Fisher Scientific), and coverslipped using Permount (Fisher Scientific).

Fluorescence immunohistochemistry was performed to co-localize GFP expression with NSE. Free-floating sections were blocked in 10% BSA for one hour at room temperature, and then incubated 48 hours at 4° C. in a solution containing mouse anti-GFP and rabbit antiNSE. Sections were incubated with Cy3 conjugated anti-mouse and FITC conjugated anti-rabbit secondary antibodies for one hour at room temperature, and coverslipped using Sigma Mounting Medium.

Other Embodiments

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A method for preparing stem cell preparations, comprising:

(a) obtaining from a postnatal mammal an epithelial tissue sample from a peripheral tissue containing sensory receptors;

(b) culturing cells dissociated from said tissue sample; and
(c) isolating from the culture multipotent cells which form non-adherent clusters in culture, are self renewing, express nestin and fibronectin, and are capable of differentiating into ectodermal and mesodermal cell types.

2. A method for preparing stem cell preparations, comprising:
(a) obtaining from a postnatal mammal an epithelial tissue sample from a peripheral tissue containing sensory receptors;
(b) separating the dermal and epidermal layers of said tissue sample;
(c) culturing cells dissociated from the dermal layer of said tissue sample;
(d) isolating from the culture multipotent cells which form non-adherent clusters in culture, are self renewing, express nestin and fibronectin, and are capable of differentiating into ectodermal and mesodermal cell types.

3. A method for preparing stem cell preparations, comprising:
(a) obtaining from a postnatal mammal an epithelial tissue sample from a peripheral tissue containing sensory receptors;
(b) culturing cells dissociated from said tissue sample;
(c) isolating from the culture multipotent cells which form non-adherent clusters in culture, are self renewing, express nestin and fibronectin, and are capable of differentiating into ectodermal and mesodermal cell types; and
(d) preserving and storing the multipotent cells for later retrieval.

4. A method for preparing cell preparations, comprising:
(a) obtaining from a patient an epithelial tissue sample from a peripheral tissue containing sensory receptors;
(b) culturing cells dissociated from said tissue sample wherein multipotent cells are expanded, which multipotent cells form non-adherent clusters in culture, are self renewing, express nestin and fibronectin, and are capable of differentiating into ectodermal and mesodermal cell types;
(c) differentiating the multipotent cells into one or more lineage committed cell types, and
(d) preserving and storing the differentiated cells for later retrieval.

5. The method of claims 3 or 4, wherein the preserved cells are formulated in a pharmaceutically acceptable carrier, auxiliary or excipient.

6. The method of claims 3 or 4, wherein the step of preserving the multipotent cells or differentiated cells includes cryogenic preservation.

7. The method of any one of claims 1-4, wherein said culturing comprises contacting said cells dissociated from said tissue sample with a therapeutic protein.

8. The method of claims 7, wherein the therapeutic protein is a growth factor.

9. The method, according to claim 8, in which the growth factor is EGF, TGF-α, or bFGF.

10. The method of any one of claims 1-4, wherein the cells are differentiated by contacting the cells with nicotinamide, RA or BMP-7.

* * * * *